(12) United States Patent
Callewaert et al.

(10) Patent No.: US 10,752,943 B2
(45) Date of Patent: Aug. 25, 2020

(54) MEANS AND METHODS FOR AMPLIFYING NUCLEOTIDE SEQUENCES

(71) Applicants: VIB VZW, Ghent (BE); UNIVERSITEIT GENT, Ghent (BE)

(72) Inventors: Nico Callewaert, Nevele (BE); Andries De Koker, Lede (BE)

(73) Assignee: VIB VZW, Ghent (BE)

(*) Notice: Subject to any disclaimer, the term of this patent is extended or adjusted under 35 U.S.C. 154(b) by 0 days.

(21) Appl. No.: 16/086,576

(22) PCT Filed: Mar. 22, 2017

(86) PCT No.: PCT/EP2017/056850
§ 371 (c)(1),
(2) Date: Sep. 19, 2018

(87) PCT Pub. No.: WO2017/162754
PCT Pub. Date: Sep. 28, 2017

(65) Prior Publication Data
US 2019/0048412 A1    Feb. 14, 2019

(30) Foreign Application Priority Data
Mar. 22, 2016  (EP) .................................. 16161672

(51) Int. Cl.
*C12Q 1/6855* (2018.01)
*C12Q 1/6853* (2018.01)
*C12N 1/00* (2006.01)

(52) U.S. Cl.
CPC ......... *C12Q 1/6855* (2013.01); *C12Q 1/6853* (2013.01)

(58) Field of Classification Search
CPC ........ C12Q 2521/319; C12Q 2521/525; C12Q 2525/301; C12Q 1/6855
See application file for complete search history.

(56) References Cited

U.S. PATENT DOCUMENTS

| | | | |
|---|---|---|---|
| 2003/0022215 A1* | 1/2003 | Makrigiorgos | C12Q 1/6827 435/6.14 |
| 2005/0202490 A1* | 9/2005 | Makarov | C12N 15/1072 435/6.12 |
| 2009/0298075 A1* | 12/2009 | Travers | C12Q 1/6869 435/6.12 |
| 2015/0133316 A1 | 5/2015 | Kirst et al. | |
| 2015/0232924 A1 | 8/2015 | Van Eijk et al. | |
| 2016/0362726 A1* | 12/2016 | Makarov | C12Q 1/6855 |

FOREIGN PATENT DOCUMENTS

| | | |
|---|---|---|
| WO | WO2009082488 | 7/2009 |
| WO | WO2012012037 A1 | 1/2012 |
| WO | WO2012092265 A1 | 7/2012 |

OTHER PUBLICATIONS

Exonuclease I, Epicentre, EPILIT059, pp. 1-3 (Year: 2012).*

(Continued)

*Primary Examiner* — Teresa E Strzelecka
(74) *Attorney, Agent, or Firm* — Patent Law Works, LLP

(57) ABSTRACT

The present invention provides methods and kits for preparing a collection of degraded DNA fragments isolated from a biofluid sample of an individual. The prepared collection of nucleic acid sequences can be used in a diagnostic method such as for example detection and/or prognosis of cancer.

8 Claims, 14 Drawing Sheets
Specification includes a Sequence Listing.

(56) References Cited

OTHER PUBLICATIONS

Exonuclease III, Epicentre, EPILIT054, pp. 1-3 (Year: 2012).*
Exonuclease VII, Epicentre, EPILIT229, pp. 1-3 (Year: 2012).*
Jin et al., Circulating Methylated DNA as Biomarkers for Cancer Detection, INTECH, Chapter 6, pp. 137-152 (Year: 2013).*
Stratagene Catalog, p. 39 (Year: 1988).*
PCT International Search Report and Written Opinion, Application No. PCT/EP2017/056850, dated May 23, 2017.
Travers et al., A flexible and efficient template format for circular consensus sequencing and SNP detection, Nucleic Acids Research, Aug. 1, 2010 Oxford University Press, GB—ISSN 1362-4962, vol. 38 pp. 1-8, Expacenet Ref NPL No. XP002615293.

* cited by examiner

DNA fragments not digested:

DNA fragments digested at 1 side:

DNA fragments digested at both sides:

DNA fragments not digested:

DNA fragments digested at 1 side:

DNA fragments digested at both sides:

+ 0,5 µL Klenow (exo-) (2,5u)
+ 1 µL CutSmart (10x)
+ 0,25 µL dNTP (1mM dCTP, dGTP, dTTP + 5mM dATP)
+ 8,25 µL H2O
---------------------------------------------------
Total: 25 µL

20' 30°C
20' 37°C
20' 75°C

DNA fragments not digested:

DNA fragments digested at 1 side:

+ 0,5 µL T4 ligase (1000 u)
+ 0,5 µL CutSmart (10x)
+ 4 µL H2O

+ 1 µL CutSmart (10x)
+ 1 µL adapter (100µM)
+ 4 µL ATP (10mM)
+ 4 µL H2O

DNA fragments digested at both sides:

ON 16°C
10' 65°C

+ 1 µL exoI (20u)
+ 0,5 µL exoIII (50u)
+ 1 µL exoVII (10u)
+ 0,5 µL CutSmart (10x)
+ 2 µL H2O
------------------------------
Total: 45 µL 2h 37°C
10' 80°C
10' 95°C

SEQUENCE LISTING

```
<160> NUMBER OF SEQ ID NOS: 11

<210> SEQ ID NO 1
<211> LENGTH: 65
<212> TYPE: DNA
<213> ORGANISM: Artificial Sequence
<220> FEATURE:
<223> OTHER INFORMATION: Adapter sequence (figure 6)

<400> SEQUENCE: 1
gatcggaaga gcacacgtct gaactccagt cuacactctt tccctacacg acgctcttcc      60
gatct                                                                  65

<210> SEQ ID NO 2
<211> LENGTH: 58
<212> TYPE: DNA
<213> ORGANISM: Artificial Sequence
<220> FEATURE:
<223> OTHER INFORMATION: Amplification primer

<400> SEQUENCE: 2
aatgatacgg cgaccaccga gatctacact ctttccctac acgacgctct tccgatct        58

<210> SEQ ID NO 3
<211> LENGTH: 64
<212> TYPE: DNA
<213> ORGANISM: Artificial Sequence
<220> FEATURE:
<223> OTHER INFORMATION: Amplification primer
```

```
<400> SEQUENCE: 3
caagcagaag acggcatacg agatcgtgat gtgactggag ttcagacgtg tgctcttccg    60
atct                                                                 64

<210> SEQ ID NO 4
<211> LENGTH: 58
<212> TYPE: DNA
<213> ORGANISM: Artificial Sequence
<220> FEATURE:
<223> OTHER INFORMATION: Primer

<400> SEQUENCE: 4
aatgatacgg cgaccaccga gatctacacu ctttccctac acgacgctct tccgatct     58

<210> SEQ ID NO 5
<211> LENGTH: 64
<212> TYPE: DNA
<213> ORGANISM: Artificial Sequence
<220> FEATURE:
<223> OTHER INFORMATION: Primer

<400> SEQUENCE: 5
caagcagaag acggcatacg agatcgtgat gtgacuggag ttcagacgtg tgctcttccg    60
atct                                                                 64

<210> SEQ ID NO 6
<211> LENGTH: 58
<212> TYPE: DNA
<213> ORGANISM: Artificial Sequence
<220> FEATURE:
<223> OTHER INFORMATION: Primer

<400> SEQUENCE: 6
aatgatacgg cgaccaccga gatctacact ctttccctac acgacgctct tccgaucu     58

<210> SEQ ID NO 7
<211> LENGTH: 64
<212> TYPE: DNA
<213> ORGANISM: Artificial Sequence
<220> FEATURE:
<223> OTHER INFORMATION: Primer

<400> SEQUENCE: 7
caagcagaag acggcatacg agatcgtgat gtgactggag ttcagacgtg tgctcttccg    60
aucu                                                                 64

<210> SEQ ID NO 8
<211> LENGTH: 65
<212> TYPE: DNA
<213> ORGANISM: Artificial Sequence
<220> FEATURE:
<223> OTHER INFORMATION: adapter

<400> SEQUENCE: 8
gatcggaaga gcacacgtct gaactccagt cuacactctt tccctacacg acgctcttcc    60
gatct                                                                65

<210> SEQ ID NO 9
<211> LENGTH: 58
<212> TYPE: DNA
<213> ORGANISM: Artificial Sequence
<220> FEATURE:
```

```
<223> OTHER INFORMATION: primer

<400> SEQUENCE: 9
aatgatacgg cgaccaccga gatctacact ctttccctac acgacgctct tccgatct        58

<210> SEQ ID NO 10
<211> LENGTH: 64
<212> TYPE: DNA
<213> ORGANISM: Artificial Sequence
<220> FEATURE:
<223> OTHER INFORMATION: primer

<400> SEQUENCE: 10
caagcagaag acggcatacg agatcgtgat gtgactggag ttcagacgtg tgctcttccg       60
atct                                                                   64

<210> SEQ ID NO 11
<211> LENGTH: 180
<212> TYPE: DNA
<213> ORGANISM: Artificial Sequence
<220> FEATURE:
<223> OTHER INFORMATION: test DNA

<400> SEQUENCE: 11
cgccagggtt ttcccagtca cgactacccg accacacggc gttgatcgcc gaggaccggc       60
gtttcacgtc gaccgagctg cgcgacgcgg tctacgcgc cgcggcggcg ctgatcgccc       120
tcggtgtcga acccgcagac cgggtggcca tctggttcct gtgtgaaatt gttatccgct     180
```

MEANS AND METHODS FOR AMPLIFYING NUCLEOTIDE SEQUENCES

FIELD OF THE INVENTION

The present invention belongs to the field of nucleic acid analysis. In particular the invention provides methods and kits for preparing a collection of degraded DNA fragments isolated from a biofluid sample of an individual. The prepared collection of nucleic acid sequences can be used in a diagnostic method such as for example detection and/or prognosis of cancer.

BACKGROUND OF THE INVENTION

In 2016 cancer will occur in more than 2 million individuals this year in the United States alone, but a clinically proven circulating biomarker that can be used to help guide patient management will be available for only a minority of them, even in the setting of widespread metastasis. Serum-based protein biomarkers such as carcinoembryonic antigen (CEA), and prostate-specific antigen (PSA) are commonly used for this purpose but these proteins are also found in the serum of individuals without cancer. Additionally, these markers are not found to be elevated in a substantial portion of patients with advanced cancers. For many years, scientists are searching for a universal biomarker to detect tumours at an early stage. Recently, a new generation of biomarkers has become available with the discovery of the genetic alterations that are responsible for the initiation and progression of human cancers. Indeed, with the increasing genomic information from cancer genome sequencing studies, it is now known that virtually all cancers of every type harbour somatic genetic alterations. These alterations include single-base substitutions, insertions, deletions, translocations (the latter including those associated with the creation of gene fusions, gene amplifications, or losses of heterozygosity) and also differentially methylated DNA-regions. Comparable somatic mutations occur at negligible frequencies in normal cell populations and therefore provide exquisitely specific biomarkers from a biological perspective. An important source of tumour DNA that can be noninvasively assessed in the circulation is cell-free circulating tumour DNA (ctDNA). This ctDNA is composed of small fragments of nucleic acid. Many studies have shown that ctDNA is present in patients having tumours, even early stage (or non-detectable tumours). The first line diagnostic methods detected mutations in single well-known oncogenes or tumor suppressor genes. Later diagnostic methods investigated multiple of these well-known genes by multiplex PCR or array-based methods. Notwithstanding these methods can detect a significant amount of tumors, it would be beneficial to have a more unbiased genome-wide view on the mutational profile of a tumor. Whole genome sequencing of the circulating free DNA sample is still very costly and data analysis is also exhaustive, so there is a need to enrich the mutation-bearing sequences. Several mutated DNA enriching techniques exist and use the rehybridization kinetic differences (C0t-analysis) between wild-type sequences and mutation-bearing sequences in combination with a mutation-sensing nuclease, DNA repair enzymes sensing mismatched sequence or duplex specific nuclease sensing completely matched sequence. All these techniques differ in nucleic acid preparation prior to denaturation-renaturation. For example, US Patent application 20030022215 uses restriction endonuclease digestion in combination with self-circularization of correctly rehybridized molecules to select against unwanted artificial mismatch rehybridization. US Patent application 20150133316 uses PCR with degenerate primers to amplify a fraction of the genome and US Patent application 20150232924 uses the AFLP technique to amplify a restriction endonuclease digested fraction of the genome. Beside the need for reducing the complexity of the sample before sequencing there is an equally important need for the reliable amplification of nuclease-sheared nucleic acid sequences such as ctDNA present in a blood sample. The present invention satisfies this need and provides methods and kits for a reliable amplification of nuclease sheared nucleic acids which are present in a biological sample. Accordingly, the invention provides an amplification technology which can be carried out in one single recipient and with one single buffer system.

SUMMARY OF THE INVENTION

In a first aspect a method is provided for preparing a collection of fragments digested with a sequence specific DNA cutting tool starting from a degraded DNA sample. The method offers a solution for the amplification of only these fragments digested with the sequence specific DNA cutting tool and not the rest of the non-digested degraded DNA. The latter has approximately the same size distribution as the degraded DNA digested with the sequence specific DNA cutting tool. The degraded DNA and the degraded DNA digested with a sequence specific DNA cutting tool cannot be separated by physical means.

In a specific aspect the degraded nucleic acid sample is purified from a biofluid and has potential use in diagnosis, in particularly the diagnosis of cancer. In a specific sample comprising DNA, the DNA is apoptotic-derived cfDNA isolated from blood plasma. In another specific aspect the DNA is purified from formalin-fixed paraffin-embedded (FFPE) tissues. It is known that such purified FFPE-DNA is highly degraded, In another specific aspect the method comprises of:
a) obtaining a nucleic acid sample of degraded DNA (e.g. cDNA, genomic DNA or cfDNA))
b) Treating said DNA with a DNA phosphatase
c) Fragmenting said dephosphorylated DNA with a sequence specific DNA cutting tool
d) Ligating adapter nucleotide sequences forming a hairpin-loop structure to the fragments obtained from said dephosphorylated DNA,
e) Treating the mixture of adapter-ligated fragments obtained from said dephosphorylated DNA with at least one exonuclease of which at least one can degrade DNA strands starting from a nick in double-stranded DNA
f) Amplifying DNA fragments using primers hybridizing at least in part to the ligated adapters.

The present invention provides in a further aspect a method to amplify sheared nucleic acids present in a sample with an average length of less than 200 nucleotides comprising the following steps:
a) dephosphorylating said sheared nucleic acids, and
b) digesting the resulting nucleic acids using at least one sequence-specific DNA cutting tool and
c) ligating the digested nucleotide sequences to hairpin looped adapters, and
d) removing incompletely ligated products, and
e) optionally opening the hairpin looped adapters present on the ligated products, and
f) amplifying the resulting nucleotide sequences using primers hybridizing to opened adapters.

In another particular aspect the nucleic acid is sheared because of physical handling of the sample. In another particular aspect the nucleic acid is sheared because of nucleases present in the sample. In a particular aspect the sheared nucleic acid is nuclease-sheared nucleic acid.

In the present invention a nucleic acid can be RNA or DNA, or a mixture of RNA and DNA.

In another particular aspect the sample is a biological sample.

In another particular aspect the biological sample is derived from a mammal such as a human. A biological sample can for example be a blood, plasma or serum sample.

In a particular aspect the sheared DNA (or in a particular aspect the nuclease-sheared DNA) is dephosphorylated with an enzyme. An example of a dephosphorylating enzyme is a nucleic acid phosphatase. Many examples of nucleic acid phosphatases exist to the skilled person. Nucleic acid phosphatases release the 5'- and 3'-phosphate groups from DNA, RNA and nucleotides. A preferred nucleic acid phosphatase is a thermosensitive nucleic acid phosphatase.

In yet another aspect a method is provided to produce a collection of nucleotide sequences from nuclease-sheared nucleotide sequences present in a biofluid sample of an organism comprising the following steps:
   a) Dephosphorylating the nucleotide sequences at the 5' ends
   b) Fragmenting the nucleotide sequences dephosphorylated at their ends using a sequence specific DNA cutting tool
   c) Ligating the phosphorylated ends of the digested nucleotide sequences to a hairpin looped adapter
   d) Enzymatically removing the non or incompletely ligated fragments
   e) Enzymatically opening the hairpin looped adapter
   f) Amplifying the remained nucleotide sequences In yet another aspect a method is provided for the diagnosis of cancer by producing a collection of nucleotide sequences from nuclease-sheared nucleotide sequences present in a biofluid sample of an organism wherein said nucleotide sequences vary from the nucleotide sequences present in the germline of said organism, the method comprising the following steps:
   a) Dephosphorylation of the 5' side of the nucleotide sequences
   b) Enzymatic fragmentation of the nucleotide sequences dephosphorylated at their ends
   c) Ligation of non-dephosphorylated ends of the digested nucleotide sequences to a hairpin looped adapter
   d) Enzymatic removal of not or incompletely ligated nucleotide sequences
   e) Enzymatic opening of the hairpin looped adapter
   f) Amplification of the obtained nucleotide sequences
   g) Selecting nucleotide sequences with mismatches by using a denaturation and renaturation step
   h) Identifying in which gene mutations are present

BRIEF DESCRIPTION OF THE DRAWINGS

MyOne™ magnetic beads using the protocol used for protein clean-up. 138 bp with both adapters trimmed shorter and 52 bp some left-over adapter

DETAILED DESCRIPTION OF THE INVENTION

Figure 1:
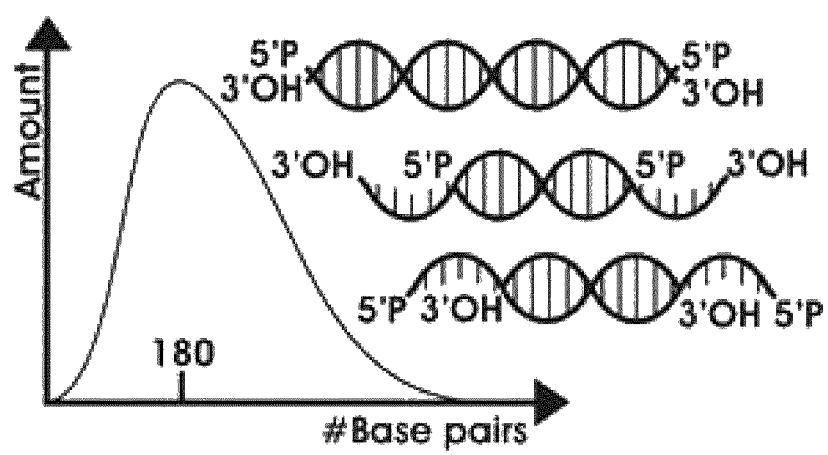
FIG. 1: Size-distribution and cartoon-representation of mechanically sheared DNA by M220 Focused Ultrasonicator (Covaris).

As used herein, each of the following terms has the meaning associated with it in this section. The articles "a" and "an" are used herein to refer to one or to more than one (i.e., to at least one) of the grammatical object of the article. By way of example, "an element" means one element or more than one element. "About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods. The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments, of the invention described herein are capable of operation in other sequences than described or illustrated herein. Unless specifically defined herein, all terms used herein have the same meaning as they would to one skilled in the art of the present invention. Practitioners are particularly directed to Sambrook et al., Molecular Cloning: A Laboratory Manual, 4$^{th}$ ed., Cold Spring Harbor Press, Plainsview, N.Y. (2012); and Ausubel et al., current Protocols in Molecular Biology (Supplement 100), John Wiley & Sons, New York (2012), for definitions and terms of the art. The definitions provided herein should not be construed to have a scope less than understood by a person of ordinary skill in the art.

Early detection is the holy grail of cancer research and any effort to enhance detection of cancer at an early stage is more than welcome. Certain fragments of DNA shed by tumours into the bloodstream can potentially be used to non-invasively screen for early-stage cancers, monitor responses to treatment and help explain why some cancers are resistant to therapies. For most tumours, a tissue biopsy is quite challenging in that it is costly, painful, or potentially risky for the patient. All these are good reasons to learn about cancer through blood and to get excited about the possibility of carrying out liquid biopsies. The development of non-invasive methods to detect and monitor tumours continues to be a major challenge in oncology. Cell-free circulating tumour DNA (ctDNA) and circulating tumour cells (CTCs) are plasma sources of tumour DNA that have been investigated for non-invasive detection and monitoring of patient tumours but have not been analysed or directly compared across multiple tumour types. Please that a more general term used in the art is circulating cell free DNA (cfDNA) which is a broader term than ctDNA since it also includes free floating DNA from non-tumor cells. Although the current Food and Drug Administration (FDA)-approved liquid biopsy measures intact CTCs to give a prognosis of overall survival, the potential predictive value of ctDNA is much more exciting. ctDNA liquid biopsy allows us to understand specifically what kind of molecular changes are happening in the tumour in real time, which is a very big step beyond where CTCs are today in clinical terms.

To date, liquid biopsies have generated a lot of excitement since they can provide a non-invasive, ongoing picture of a patient's cancer, offering valuable insight into how best to fight it. In addition to offering clues about stage and spread, liquid biopsies can be used to monitor the effects of cancer treatment, give an early warning about possible recurrence and offer clues to the reasons for treatment resistance. ctDNA investigations in cancer patients are increasingly being performed, supporting the different potential applications of this approach. Serial analysis of ctDNA during treatment can provide a dynamic picture of molecular disease changes, suggesting that this non-invasive approach could also be used to monitor the development of secondary resistance and identify heterogeneous subclonal populations of tumour cells developing during the course of treatment. In the future, instead of extensive imaging and invasive tissue biopsies, liquid biopsies could be used to guide cancer treatment decisions and perhaps even screen for tumours that are not yet visible on imaging.

The problem to amplify minute amounts of sheared DNA present in human samples has been solved in the present invention. Accordingly, the invention provides an amplification technology which can be carried out in one single recipient and with one single buffer system. In addition, the method of the invention generates a collection of DNA fragments digested with a sequence specific DNA cutting tool starting from a nucleic acid sample which is degraded to such extent that degraded DNA and said degraded DNA digested with the sequence specific DNA cutting tool cannot be resolved by physical means.

Accordingly, in a first embodiment the invention provides a method to amplify sheared nucleic acids present in a sample with an average length of less than 200 nucleotides comprising the following steps:
  a) dephosphorylating said sheared nucleic acids, and
  b) digesting the resulting nucleic acids using at least one sequence specific DNA cutting tool, and
  c) ligating the digested nucleotide sequences to hairpin looped adapters, and d) removing incompletely ligated products, and
e) amplifying the resulting nucleotide sequences using primers hybridizing to opened adapters.

In a particular embodiment the nucleic acid is sheared because of physical handling of the sample. In another particular embodiment the nucleic acid is sheared because of nucleases present in the sample. In a particular embodiment the sheared nucleic acid is nuclease-sheared nucleic acid.

In the present invention a nucleic acid can be RNA or DNA, or a mixture of RNA and DNA. In another embodiment the nucleic acid is methylated. In a particular embodiment when the nucleic acid is RNA it needs to be modified to copy DNA (cDNA).

In another particular embodiment the sample is a biological sample.

In another particular embodiment the biological sample is derived from a mammal such as a human. A biological sample can for example be a blood, plasma or serum sample.

In a particular embodiment the sheared DNA (or in a particular embodiment the nuclease-sheared DNA) is dephosphorylated with an enzyme. An example of a dephosphorylating enzyme is a nucleic acid phosphatase. Many examples of nucleic acid phosphatases exist to the skilled person. Nucleic acid phosphatases release the 5'- and 3'-phosphate groups from DNA, RNA and nucleotides.

A preferred nucleic acid phosphatase is a thermosensitive nucleic acid phosphatase. Thus in a particular embodiment the nucleic acid phosphatase used is a heat-labile phosphatase but needs the addition of a cofactor to be active (e.g. Antarctic Phosphatase), so no purification is necessary to deplete the enzyme. In yet another particular embodiment the nucleic acid phosphatase is a heat-labile phosphatase and needs no addition of a cofactor to be active (e.g. recombinant Shrimp Alkaline Phosphatase).

In yet another specific embodiment calf Intestinal Phosphatase is used but purification is necessary to deplete the enzyme.

In a particular embodiment the dephosphorylated nucleic acids are digested with a restriction enzyme. In another particular embodiment the dephosphorylated nucleic acids are digested with a restriction enzyme recognizing a specific tetranucleotide sequence (a tetranucleotide recognizing enzyme or a tetracutter enzyme). In another specific embodiment the dephosphorylated nucleic acids are digested with a restriction enzyme recognizing a specific penta-nucleotide sequence (a penta-nucleotide recognizing enzyme or a pentacutter enzyme). In another specific embodiment the dephosphorylated nucleic acids are digested with a restriction enzyme recognizing a specific hexa-nucleotide sequence (a hexa-nucleotide recognizing enzyme or a hexacutter enzyme). In another specific embodiment the dephosphorylated nucleic acids are digested with a restriction enzyme recognizing a specific 7-nucleotide sequence (a 7-nucleotide recognizing enzyme or a 7-cutter enzyme). In another specific embodiment the dephosphorylated nucleic acids are digested with a restriction enzyme recognizing a specific 8-nucleotide sequence (a 8-nucleotide recognizing enzyme or a 8-cutter enzyme). In yet another specific embodiment the at least one restriction enzyme is a mixture of two or more restriction enzymes (e.g. a 4-cutter and a 5-cutter, or a 4-cutter and a 6-cutter enzyme). In yet another specific embodiment the restriction enzyme is a methylation insensitive enzyme. Indeed, many restriction enzymes are sensitive to the DNA methylation states and cleavage may be blocked, or impaired, when a particular base in the enzyme's recognition site is methylated.

In a particular embodiment the nucleic acids fragmented with at least one restriction enzyme are ligated with adapter sequences. In another preferred embodiment said adapter sequences are hairpin looped adapters. A hairpin (or hairpin loop or a stem-loop structure) is a pattern that occurs when two regions of the same strand, usually complementary in nucleotide sequence when read in opposite directions, basepair to form a a double helix that ends in an unpaired loop. In another particular embodiment the hairpin-looped adapter is linked by a chemical, protein, nucleic acid linker, but may not interfere with the subsequent exonuclease activity An example of an adapter sequence is depicted below in SEQ ID NO: 1. It contains a 5' phosphate group, an internal deoxyUracil nucleotide and a 3' T-overhang. The adapter is a looped structure due to 12 bp of complementarity between 5' and 3'.

```
SEQ ID NO: 1:
5'P-GATCGGAAGAGCACACGTCTGAACTCCAGTC/deoxyU/
ACACTCTTTCCCTACACGACGCTCTTCCGATCT-3'
```

SEQ ID NO: 2 and 3 represent amplification primers, complementary to the two parts of the adapter. Here the primers contain a phosphorothioate bond (marked by *) at the 3' end to avoid hydrolysis of the 3' base but primers without a phosphorothioate bond also work. The primers are used to extent the library fragments with the appropriate sequencing features, distal features for binding to the Illumina-chip, index-sequence (underlined) for multiplexing, and features close to the insert for sequencing purposes.

```
SEQ ID NO: 2:
5'-AATGATACGGCGACCACCGAGATCTACACTCTTTCCCTACACGACGC
TCTTCCGATC*T-3'

SEQ ID NO: 3:
5'-CAAGCAGAAGACGCCATACGAGATCGTGATGTGACTGGAGTTCAGAC
GTGTGCTCTTCCGATC*T-3'
```

This library contains long adapter-sequences, this can be problematic during normalization as these high abundant sequences will dominate the normalization process. That is why shorter adapter sequences are advisable. The idea was to cut a piece of the commercial adapter to truncate these to a length compatible with normalization.

Figure 14:
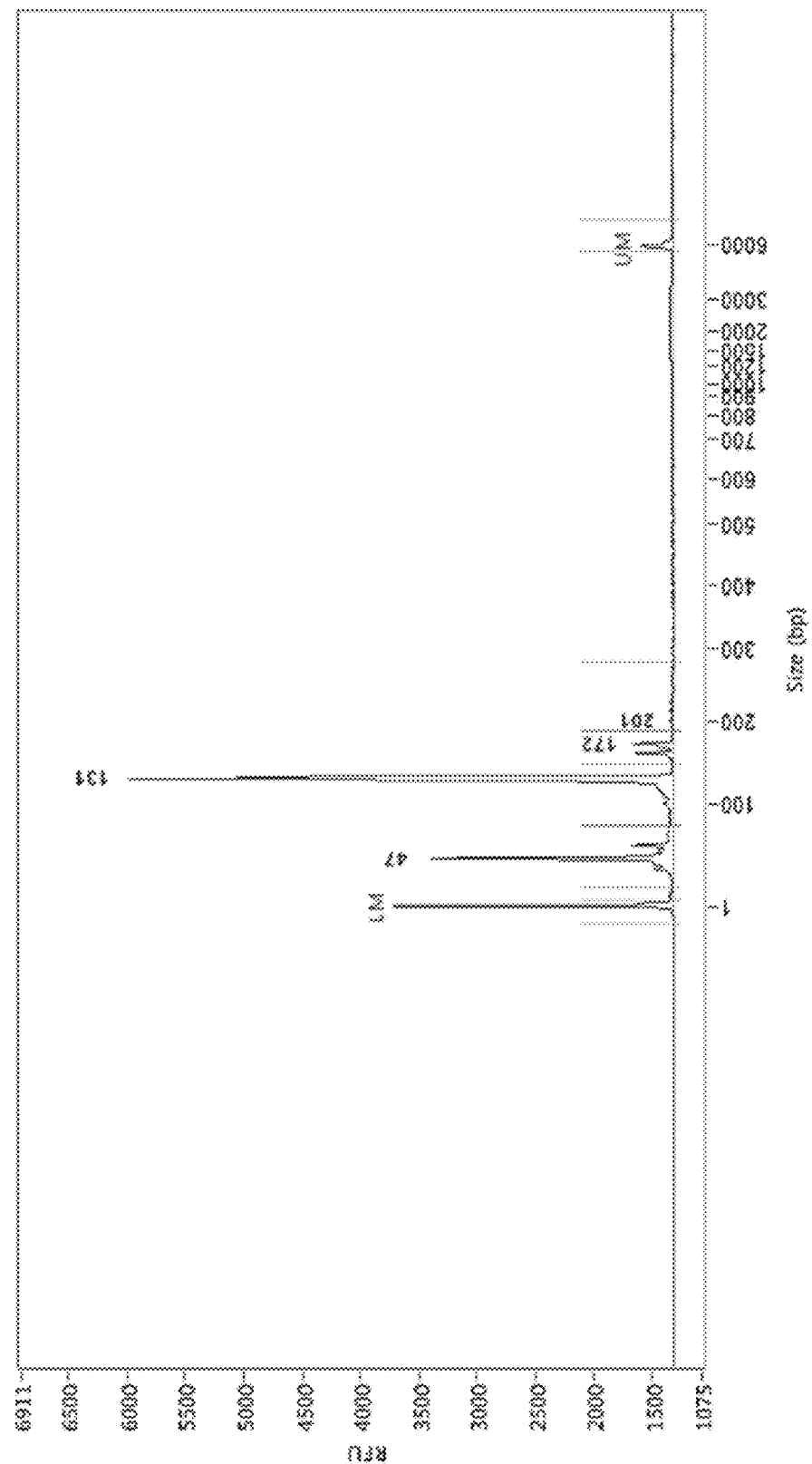
FIG. 14: SEQ ID NO 11 prepared using the RRBS amplification protocol and amplified with normalization primers (SEQ ID NO: 4 and SEQ ID NO: 5). The amplification product was incubated with Antarctic UDG, endonuclease VIII and T7 endonuclease I in CutSmart. Product of 201 bp is full-length, 172 bp with one adapter trimmed off, 131 bp with both adapters trimmed off and 47 bp the pieces of the adapter.
Figure 15:
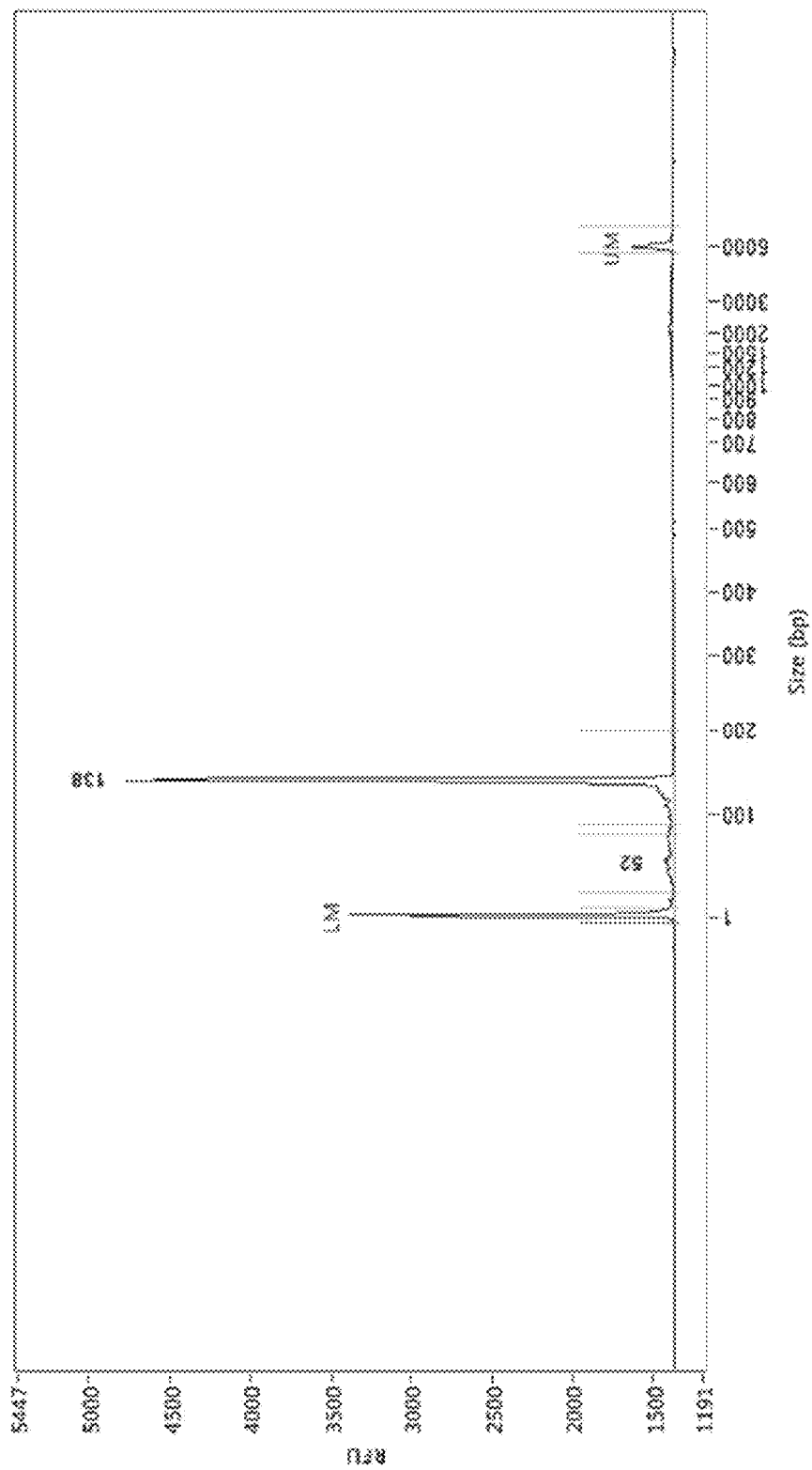
FIG. 15: The adapter-trimmed mixture (FIG. 13) was cleaned up by use of streptavidin linked to Dynabeads™
Figure 16:
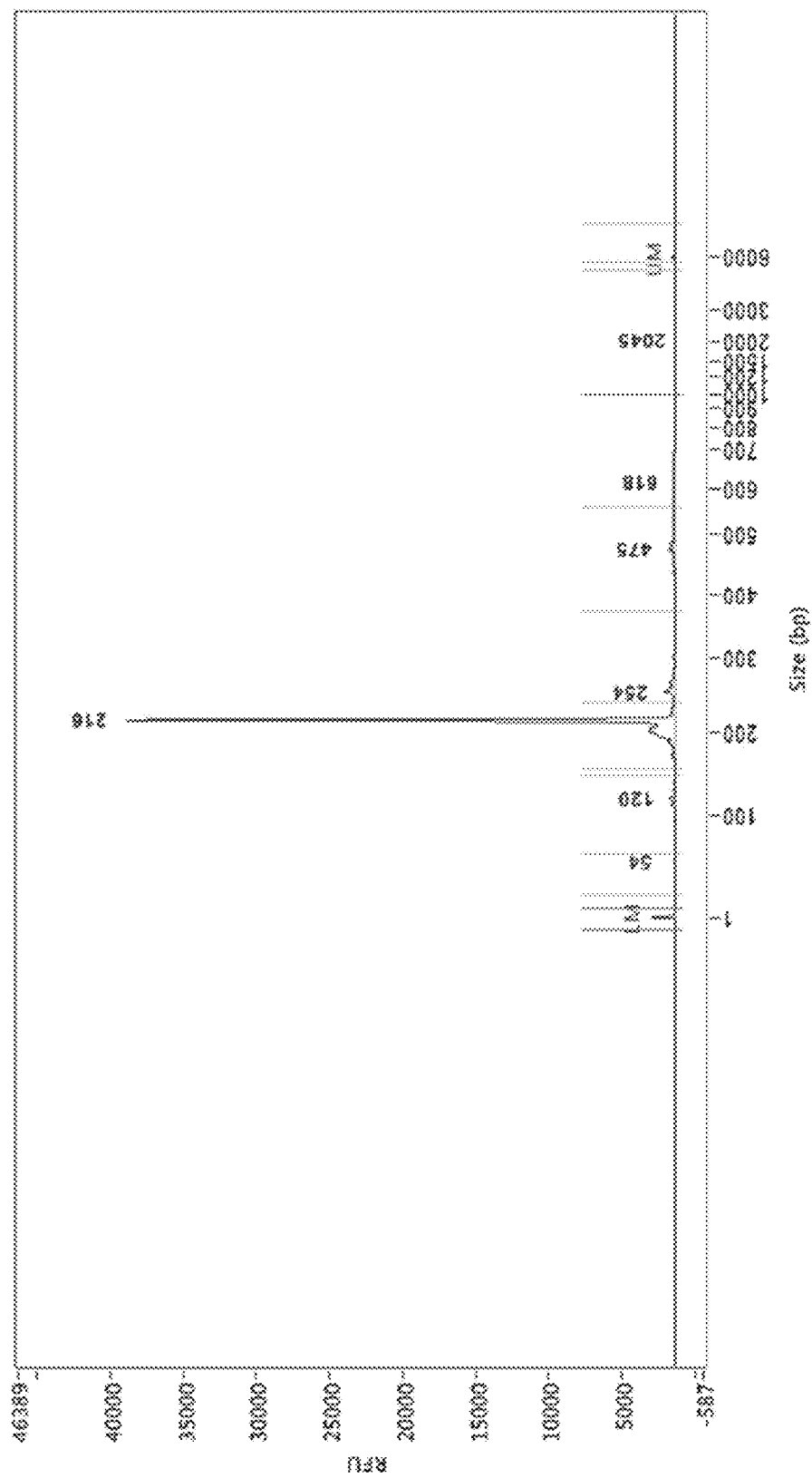
FIG. 16: 100 ng of cleaned-up mixture (FIG. 14) was reamplified using commercial NEBNext primers with 2×KAPA HiFi U+ polymerase

By PCR a uracil is incorporated in the middle of the adapter in both strands using primers SEQ ID NO: 4 and SEQ ID NO: 5. By the use of a three-enzyme mixture: Antarctic Thermolabile UDG, Endonuclease VIII and T7 endonuclease I a double stranded break is generated at the site a uracil was incorporated (FIG. 14). Because T7 endonuclease I is not heat-denaturable proteinase K was added and after incubation the proteinase K was killed by heat. The end-pieces of the adapters were removed by use of Dynabeads™ MyOne™ magnetic beads and immobilizing in PBS. As a result you end up with a DNA-library with truncated adapter in a mixture of chopped-up and heat-denatured enzymes dissolved in PBS/CutSmart (FIG. 15). This mixture can be used in the Duplex-specific nuclease reaction. After DSN the library is single-stranded and has to be amplified, this is done using the commercial NEBNext primers (FIG. 16).

SEQ ID NO: 4:
5'-Biotin-AATGATACGGCGACCACCGAGATCTACAC/ideoxyU/

CTTTCCCTACACGACGCTCTTCCGATCT-3'

SEQ ID NO: 5:
5'-Biotin-CAAGCAGAAGACGGCATACGAGATCGTGATGTGAC/ ideoxyU/GGAGTTCAGACGTGTGCTCTTCCGATCT-3'

The rationale of using driver DNA is to make the efficiency of the normalization process less dependent on the amount of tumor-derived cfDNA. Adding an excess of patient germline DNA to the DSN reaction could push the normalization reaction towards enrichment of rare and non-germline DNA. The driver DNA should be treated the same way the cfDNA is treated, but for the same reason as above it is now advisable to have no adapter sequences present as we do not want to amplify our driver DNA at the end of the normalization reaction.

SEQ ID: 6:
5'-Biotin-AAT GAT ACG CCC ACC ACC GAG ATC TAC ACT

CTT TCC CTA CAC GAC GCT CTT CCG A*/ideoxyU/*C*/

3ideoxyU/-3'

SEQ ID: 7:
Biotin NEBNext index 1 3U*: 5'-Biotin-CAA GCA GAA

GAC CCC ATA CGA GAT CGT GAT CTC ACT GGA GTT CAG ACG

TGT GCT CTT CCG A*/ideoxyU/*C*/3ideoxyU/-3'

Figure 17:
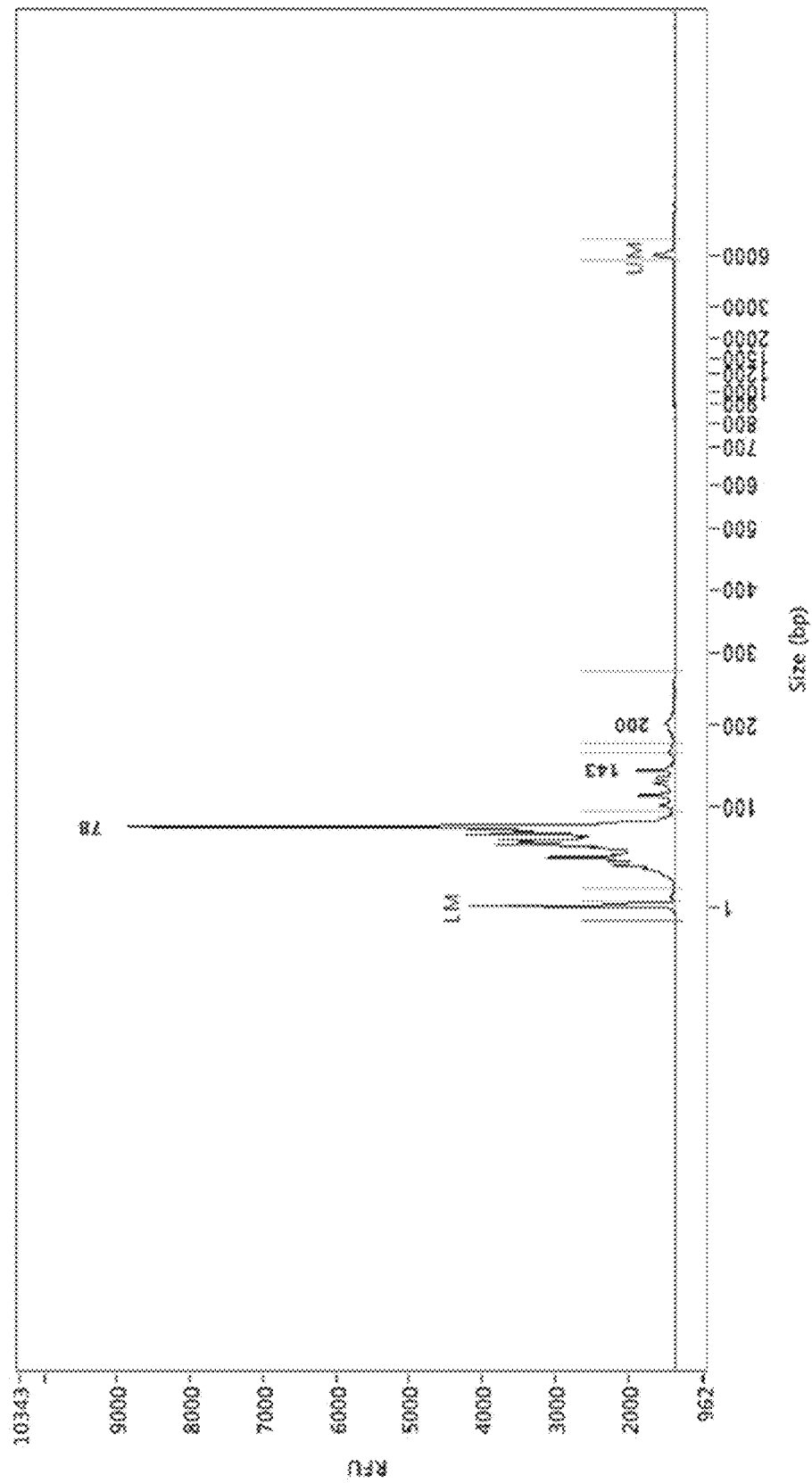
FIG. 17: SEQ ID NO 11 prepared using the RRBS amplification protocol and amplified with driver DNA primers (SEQ ID NO: 6 and SEQ ID NO: 7). The amplification product was incubated with Antarctic UDG, endonuclease VIII and T7 endonuclease I in CutSmart. Product of 200 bp is full-length, 143 bp with one adapter trimmed off, 78 bp with both adapters trimmed off.
Figure 18:
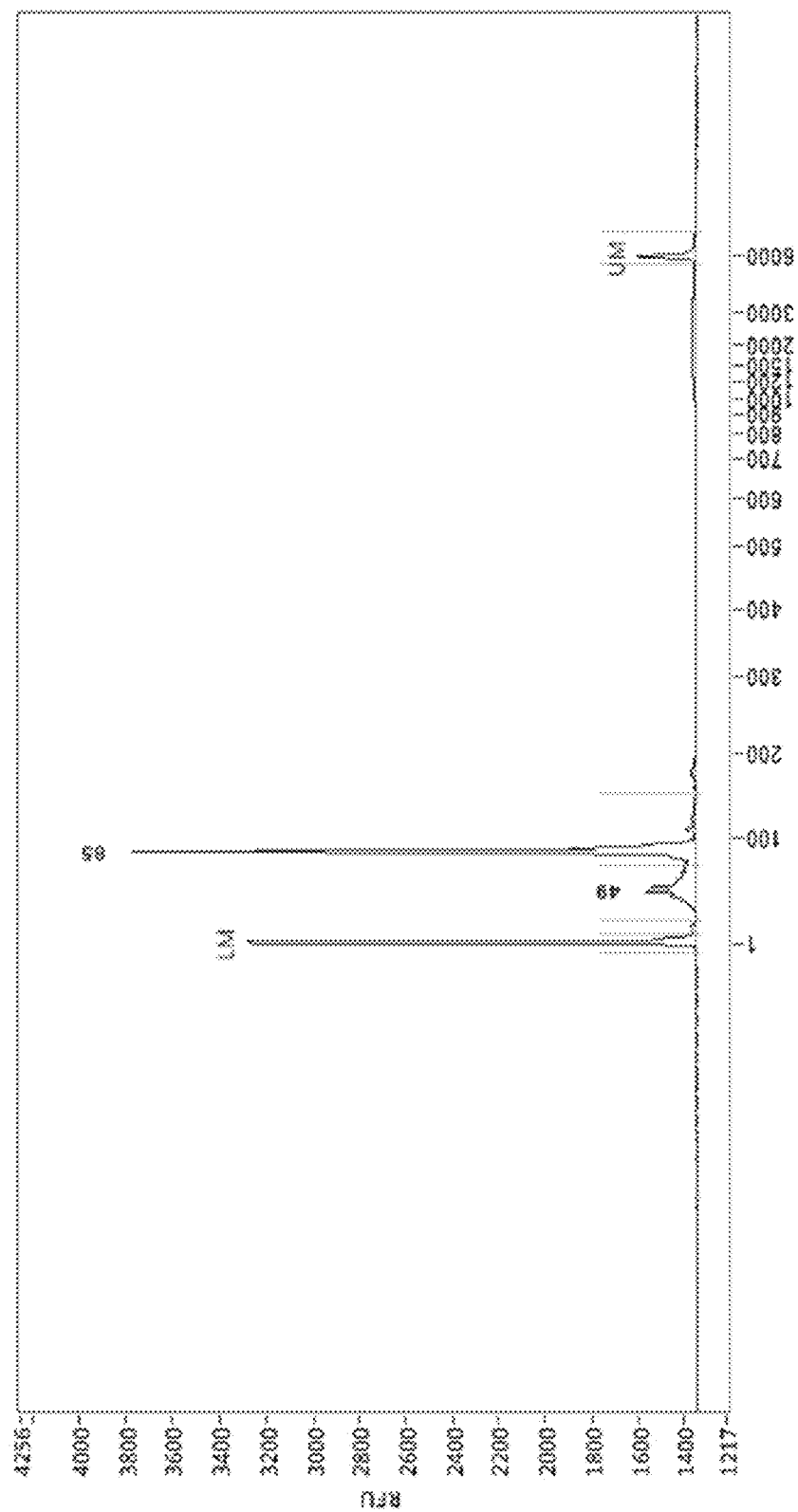
FIG. 18: The adapter-trimmed mixture (FIG. 16) was cleaned up by use of streptavidin linked to Dynabeads™ MyOne™ magnetic beads using the protocol used for protein clean-up. 85 bp is the insert and 49 bp probably some leftover adapter.

By PCR two uracils and three phosphorothiate bonds were incorporated 3' end because the proofreading activity of the KAPA polymerase can chop of the uracil-bases. By the use of a three-enzyme mixture: Antarctic Thermolabile UDG, Endonuclease VIII and T7 endonuclease I a double stranded break is generated at the site the uracils were incorporated (FIG. 17). Because T7 endonuclease I is not heat-denaturable proteinase K was added and after incubation the proteinase K was killed by heat. The end-pieces of the adapters were removed by use of Dynabeads™ MyOne™ magnetic beads and immobilizing in PBS. As a result one ends up with a DNA-library with truncated adapter in a mixture of chopped-up and heat-denatured enzymes dissolved in PBS/CutSmart (FIG. 18). This mixture can be used in the Duplex-specific nuclease reaction.

In another embodiment the invention provides a method to amplify sheared nucleic acids present in a sample with an average length of less than 200 nucleotides comprising the following steps:
a) dephosphorylating said sheared nucleic acids, and
b) digesting the resulting nucleic acids using at least one sequence specific DNA cutting tool, and
c) ligating the digested nucleotide sequences to hairpin looped adapters, and
d) removing incompletely ligated products, and
e) opening the hairpin looped adapters present on the ligated products, and
f) amplifying the resulting nucleotide sequences using primers hybridizing to opened adapters.

In yet another embodiment the invention provides a method to amplify sheared nucleic acids present in a sample with an average length of less than 200 nucleotides comprising the following steps:

a) dephosphorylating said sheared nucleic acids, and
b) digesting the resulting nucleic acids using at least one sequence specific DNA cutting tool, and
c) adding a dA-tailing polymerase,
d) ligating the digested nucleotide sequences to hairpin looped adapters, and
e) removing incompletely ligated products, and
f) opening the hairpin looped adapters present on the ligated products, and
g) amplifying the resulting nucleotide sequences using primers hybridizing to opened adapters.

In a particular embodiment the at least one restriction enzyme used in the methods generates 3' overhang ends after cleavage of the nucleic acids in the sample. In this event the combination of Klenow enzyme followed by the addition of Klenow (exo-minus) is used. The Klenow fragment serves to provide end-repair of generated 3' overhang. The Klenow fragment is a large protein fragment produced when DNA polymerase I from *E. coli* is enzymatically cleaved by the protease subtilisin. The Klenow fragment retains the 5'→3' polymerase activity and the 3'→5' exonuclease activity for removal of precoding nucleotides and proofreading, but loses its 5'→3' exonuclease activity. Before adding Klenow (exo-minus), the large Klenow fragment has to be removed by clean-up or by adding a thermolabile protease (e.g. proteinase K). In a next step the Klenow (exo-minus) is used which generates dA tailing of the fragments.

In yet another embodiment the at least one restriction enzyme used in the methods generates 5' overhang ends. In this event a convenient dA-tailing polymerase is the Klenow (exo-minus or exo-) enzyme is used which provides fill in of the 5' overhang ends followed by dA-tailing of the fragments. Exo-minus Klenow DNA Polymerase is a DNA-dependent polymerase that lacks both the 5'→3' and the 3'→5' exonuclease activities of DNA polymerase I, from which it is derived. This N-terminal truncation of DNA polymerase I has two mutations (D355A and E357A).

In yet another embodiment the incompletely ligated products (id est the ligated digested nucleotide sequences to hairpin looped adaptors) are removed by at least one exonuclease which exonuclease degrades DNA strands starting from a nick in double stranded DNA. In another particular embodiment the incompletely ligated products (id est the ligated digested nucleotide sequences to hairpin looped adaptors) are removed by a mixture of exonucleases. In a particular embodiment said mixture of exonucleases comprises exonuclease I, III and VII.

Exonuclease I catalyzes the removal of nucleotides from single-stranded DNA in the 3' to 5' direction. Exonuclease III, catalyzes the stepwise removal of mononucleotides from 3' hydroxyl termini of duplex DNA. The preferred substrates are blunt or recessed 3' termini, although the enzyme also acts at nicks in duplex DNA to produce single-strand gaps. The enzyme is not active on ssDNA, and thus 3' protruding termini are resistant to cleavage. Exonuclease VII, (Exo VII) derived from *E. coli*, cleaves single-stranded DNA (ssDNA) from both 5'→3' and 3'→5' direction. This enzyme is not active on linear or circular dsDNA. It is for example useful for removal of single stranded oligonucleotide primers from a completed PCR reaction when different primers are required for subsequent PCR reactions.

In yet another embodiment the obtained ligated digested nucleotide sequences with the hairpin looped adaptors are enzymatically opened before the amplification step.

Opening of the ligated adapter-fragments is recommended since it enhances the efficiency of the optional bisulfite conversion. In addition, opening of the adaptor increases the efficiency of amplification. In a particular embodiment when the hairpin adaptors are not opened primers can be used which bind the loop-region of the adapter in combination with a polymerase with strand-displacement activity. In a particular embodiment the opening of the adapters is carried out with an uracil-DNA glycosylase enzyme. This enzyme catalyzes the release of free uracil from uracil-containing single-stranded or double stranded DNA. The resulting a-basic sites are susceptible to hydrolytic cleavage at elevated temperature and high pH. In a preferred embodiment the uracil-DNA glycosylase is thermolabile. In a specific embodiment the thermolabile UDG is the Antarctic thermolabile Uracil-DNA glycosylase. In a particular embodiment the opening of the adapters by an uracil DNA-glycosylase is followed by an endonuclease VIII treatment. A convenient source is the endonuclease VIII from E. coli acts as both an N-glycosylase and an AP-lyase. The N-glycosylase activity releases damaged pyrimidines from double-stranded DNA, generating an apurinic (AP site). The AP-lyase activity cleaves 3' and 5' to the AP site leaving a 5' phosphate and a 3' phosphate.

In yet another embodiment before the amplification step a sodium bisulfite treatment is applied.

DNA methylation, which most commonly occurs at the C5 position of cytosines within CpG dinucleotides, plays a pivotal role in many biological procedures such as gene expression, embryonic development, cellular proliferation, differentiation and chromosome stability. Aberrant DNA methylation is often associated with loss of DNA homeostasis and genomic instability leading to development of human diseases such as cancer. The importance of DNA methylation creates an urgent demand for effective methods with highly sensitivity and reliability to explore innovative diagnostic and therapeutic strategies. Bisulfite genomic sequencing developed by Frommer and colleagues was recognized as a revolution in DNA methylation analysis based on conversion of genomic DNA by using sodium bisulfite. Besides various merits of the bisulfite genomic sequencing method such as being highly qualitatively and quantitatively, it serves as a fundamental principle to many derived methods to better interpret the mystery of DNA methylation. Here we will present a protocol currently frequently used in our laboratory that has proved to yield optimal outcomes. Several methods are available in the art which can be used for bisulphite treatment. One DNA methylation detection protocol is published by Li Y. and Toffefsbol T. O. (2011) Methods Mol. Biol. 791: 11-21. In addition, several commercial kits are available for sodium bisulfite treatment such as for example the kits distributed by Qiagen and ZymoResearch.

In yet another embodiment the optional bisulfite treatment step is followed by an amplification step. In specific embodiments high-fidelity polymerases can be used where no bisulphite treatment occurred (e.g. Phusion polymerase, Q5-polymerase, KAPA HiFi polymerase). In another particular embodiment where bisulfite conversion is performed other polymerases have to be used that can readily incorporate nucleotides facing the uracil-bases (e.g. Kapa HiFi uracil+polymerase).

A method to produce a collection of nucleotide sequences from nuclease-sheared nucleotide sequences present in a biofluid sample of an organism comprising the following steps:
a) Dephosphorylating the nucleotide sequences at the 5' ends
b) Fragmenting the nucleotide sequences dephosphorylated at their ends using an enzyme leaving a 5' phosphate group
c) Ligating the phosphorylated ends of the digested nucleotide sequences to a hairpin looped adapter
d) Enzymatically removing incompletely ligated products
e) Enzymatically opening the hairpin looped adapter
f) Amplifying the remained nucleotide sequences In yet another embodiment a normalization or a c0t-derived protocol comprising of a denaturation step, a renaturation step and using any agent that recognizes the site of the mismatch is applied on the amplified nucleotide sequences. A normalization protocol seriously reduces the cost for sequencing and data analysis because the nucleotide sequences are enriched for mutation carrying nucleotide sequences.

An important approach, high-$C_0t$ analysis (where "$C_0$" is DNA concentration at time zero and "t" is re-association time), is based on DNA renaturation kinetics. Because low-copy DNA sequences harbouring mutations, not present in the germline, renature more slowly than more abundant sequences, a ssDNA fraction of high-$C_0t$ DNA enriched with tumor mutations can be obtained under suitable conditions. In this technique, amplified DNA obtained via the method of the invention is heat-denatured, and slowly re-annealed. Then, the double-stranded (more abundant) somatic DNA can be separated from the single-stranded (low-copy) DNA from tumors by hydroxyapatite (HAP) chromatography. High-$C_0t$ analysis can be applied to any sample; however, practitioners generally need a firm understanding of DNA reassociation kinetics and relatively advanced expertise in spectrophotometry. While we do not exclude the possibility of the previous method in the present invention, we recommend the application of duplex-specific nuclease (DSN) normalization technology for eukaryotic genomic DNA. The method is based on the properties of a DSN isolated from the Kamchatka crab. DSN is thermostable and specific to dsDNA. Like high-$C_0t$ DNA fractionation, DSN normalization is based on hybridization kinetics, but does not involve physical separation of ssDNA and dsDNA fractions. After re-association of denatured DNA, dsDNA comprising somatic sequences is hydrolyzed by DSN and the ssDNA fraction containing low-copy molecules, harbouring tumor mutations, is amplified by PCR.

In a particular aspect, instead of using DSN normalization to deplete highly repetitive sequences and to avoiding to sequence these regions, also more targeted approaches are available.

Removal of repetitive sequences can be done by adding oligonucleotides to the sample which are complementary to the most abundant DNA fragments. After denaturation and hybridization of such oligonucleotides to the DNA present in the sample DNA-oligonucleotide duplexes are formed. These DNA-oligonucleotide duplexes can be cut by DSN. Alternatively, the oligonucleotides can be labeled with a feature (e.g. biotin) which can be pulled out to deplete the DNA-oligo duplex.

In another aspect also CRISPR-cas9 in combination with sgRNAs complementary to repetitive DNA fragments can be used to specifically deplete these sequences. An absolute requirement in this CRISPR-cas9 system is the availability of a PAM-sequence (see Gu W. et al (2016) Genome Biology 17:41). As a non-limiting example in the case MspI is used as a restriction enzyme it is possible to include the PAM-sequence in the adapter and use every sequence next to an MspI-site as guide-sequence, which would make our method less dependent on available PAM-sequences in the human genome to deplete specific DNA fragments.

In yet another aspect to make the efficiency of the normalization procedure less dependent on the percentage of circulating tumor DNA in total circulating free DNA, an excess of germline driver DNA can also be added to the sample. Driver DNA can be generated from genomic DNA of blood cells. Driver DNA is processed completely the same way as the cfDNA sample, except that it is amplified with primers containing the A*U*C*U sequence at the 3' end of the amplification primers. This sequence can be broken at both strands using the enzyme mixture: Antarctic Thermolabile UDG, Endonuclease VIII and T7 endonuclease. Because T7 endonuclease I is not heat-denaturable proteinase K was added and after incubation the proteinase K was killed by heat. The end-pieces of the adapters were removed by use of Dynabeads™ MyOne™ magnetic beads and immobilizing in PBS. As a result you end up with a DNA-library with no adapter in a mixture of chopped-up and heat-denatured enzymes dissolved in PBS/CutSmart. This mixture can be used in the Duplex-specific nuclease reaction, so adapter sequences can be removed after bisulfite conversion and subsequent amplification without degrading the patient DNA sample. Adapter sequences should be removed to avoid that they will dominate the normalization procedure and to avoid that driver DNA will be sequenced. An additional step to remove driver DNA after normalization is the use of 5' phosphorylated primers for driver DNA amplification and the use of 5' phosphorothioate containing primers for cfDNA amplification. The combination of these two kinds of primers makes it possible to degrade specifically driver DNA and not cfDNA by lambda exonuclease. Lambda exonuclease removes mononucleotides from duplex DNA in a 5' to 3' direction. The preferred substrate is 5' phosphorylated double stranded DNA, although it will also degrade single-stranded and non-phosporylated substrates at a reduced rate. Lambda exonuclease has no significant activity to phosphorothioate bonds.

In yet another embodiment the invention provides a method of diagnosis of cancer by producing a collection of nucleotide sequences from nuclease-sheared nucleotide sequences present in a biofluid sample of an organism wherein said nucleotide sequences vary from the nucleotide sequences present in the germline of said organism, the method comprising the following steps:
  a) Dephosphorylation of the 5' side of the nucleotide sequences
  b) Enzymatic fragmentation of the nucleotide sequences dephosphorylated at their ends
  c) Ligation of non-dephosphorylated ends of the digested nucleotide sequences to a hairpin looped adapter
  d) Enzymatic removal of not or incompletely ligated nucleotide sequences
  e) Enzymatic opening of the hairpin looped adapter
  f) Amplification of the obtained nucleotide sequences
  g) Selecting nucleotide sequences with mismatches by using a denaturation and renaturation step
  h) Sequencing the obtained nucleotide sequences and identifying in which gene mutations are present A variety of sequencing methods are known to the person skilled in the art. A preferred sequencing technology is the illumina sequencing technology.

In yet another embodiment the invention provides for a diagnostic method for the detection or the prognosis of cancer comprising any of the previous methods described herein before followed by the application of a normalization step to enrich for variant nucleotide sequences, sequence determination of said variant nucleotide sequences and correlating the sequence variations with a detection or a prognosis of cancer.

In yet another embodiment the invention provides a kit for amplifying sheared DNA with an average length of less than 200 nucleotides comprising a DNA phosphatase, at least one sequence specific DNA cutting tool, exonucleases I, III and VII, Klenow enzyme and Klenow enzyme (exo-minus), deoxynucleotide bases, hairpin looped adapters, primers specific for the hairpin looped adapters, a DNA polymerase and a buffer system.

The following examples are intended to promote a further understanding of the present invention. While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

EXAMPLES

1. General Description of the Amplification Technology
1.1 Isolating the Nucleic Acids from a Biofluid Sample On any given moment, cells are dying in the body for various reasons. In a healthy individual most cell death occurs because these cells are old and have to be replaced by new cells. These cells shed their genomic DNA into the bloodstream as circulating free DNA. This circulating free DNA is highly fragmented due to the process of apoptosis and further endo- and exonuclease activity. It is known that when developing a tumor in the body, a higher amount of circulating free DNA is shed into the bloodstream, this because more cell death occurs in tumor tissue due to lethal mutagenesis and uncontrolled cell growth. Also this tumor DNA is shed into the bloodstream, making this collection of circulating free DNA fragments a highly valuable biosample for the non-invasive biopsy of the total body. First a Medical Doctor collects a sufficient amount of blood of an individual. As the amount of circulating free DNA is low, collecting some milliliters (e.g. a widely used volume is 10 mL) of blood is necessary. Recently it is claimed that 100-200× more cfDNA could be extracted from blood plasma, making it possible to extract enough cfDNA from a drop of blood (Circulogene) The blood has to be collected in a vacutainer with a cell-stabilizing agent and anti-coagulant, such as EDTA, to avoid genomic DNA leakage from blood cells. At the moment the most optimal vacutainers are distributed by STRECK or PreAnalytiX, which contain formaldehyde-free conservatives. In the optimal embodiment the method is performed with UV-sterilized material to avoid contamination with foreign DNA. Also the use of LoBind-tubes is preferred. In alternative vacutainers, other blood plasma collection methods and other ways of extracting the cfDNA can lead to a similar result. The most optimal biofluid is blood plasma, due to low contamination of the targeted DNA by dying blood cells. The Early Detection Research Network, part of the National Cancer Institute, published a standard operation procedure for collection of blood plasma and can be found here: https://edrn.nci.nih.gov/resources/standard-operating-procedures/standard-operating-procedures/plasma-sop.pdf. In a next step the circulating free DNA needs to be purified from the blood sample. At the moment some kits are available to purify this cfDNA but two kits can cope with high volume (>1 mL) input. The QIAamp Circulating Nucleic Acid Kit(Qiagen) can purify shorter fragments (>75 bp) in comparison with the Quick-cfDNA™

Serum & Plasma Kit (ZymoResearch) (>100 bp), but the yield of the Zymoresearch kit will probably be higher due to column design.

1.2 Dephosphorylating the 5' Side of the Collection of Nucleic Acids with a Phosphatase As this method can be used as part of a diagnostic method, purification or buffer exchange steps are preferably avoided. Recombinant Shrimp Alkaline Phosphatase is a heat-labile phosphatase, distributed by NEB and works in the semi-universal buffer CutSmart™.

1.3 Fragmenting the Dephosphorylated DNA with a Sequence Specific DNA Cutting Tool It is necessary that the sequence specific DNA cutting tool leaves a 5' phosphate. The most common cutting tools are restriction enzymes, but also a system making use of the cas9-nuclease and a guide RNA or similar could be used. In the optimal embodiment the cutting tool works 100% in the CutSmart™ buffer and leaves behind a single overhang 3'-dA, but also blunt-ends or 5'-overhangs are easy to work with.

1.4 End-Repair and dA-Tailing of the Dephosphorylated DNA Fragments

If in the previous step a single 3'-dA end is generated, this step can be skipped. If a blunt-end or 5'-overhang is generated the addition of Klenow(exonuclease minus) in presence of all dNTP's (prepared as fresh as possible) is sufficient to fill-in the ends and dA-tail in a single step. If a 3'-overhang, other than a 3'-dA is generated, a two-step process in needed. First DNA polymerase I, large (Klenow) fragment in combination with all dNTP's is used to generate a blunt end. After removal (by purification or proteolysis with proteinase K) of the DNA polymerase I, large (Klenow) fragment, dA-tailing is done by addition of Klenow (exonuclease minus) in presence of dATP. Important when working in the same reaction vessel without purification is to add sufficient dNTP's, especially dATP, so the Klenow(exo-) fragment can work (Km=1-2 μM) but not too much because dATP inhibits T4 DNA ligase (Ki=35 μM).

1.5 Ligating Adapter Sequences to the Fragments Obtained from Said Dephosphorylated DNA It is necessary that the adapter consists of two nucleic acid sequences which are linked together to a closed form with an exonuclease degradable feature (e.g. containing an uracil base). In an optimal working mode the hairpin-looped adapter is an adapter compatible with a widely used Next Gen Sequencing platform, e.g. Illumina and the adapter can be opened to enhance further amplification. An optimal adapter is the adapter sold by New England Biolabs, the NEBNext adapter (but without the 3' phosporothioate bond). If the sample is subsequently bisulfite treated, all cytosines have to be methylated. The optimal ligase in library preparation is the T4 DNA ligase and works in the CutSmart™ buffer when 10 mM ATP (prepared as fresh as possible) is added. It is advised to add an excess (100:1) of adapter (annealed in CutSmart™ as fresh as possible) to preserve the diversity of the library.

1.6 Removal of Non- or Partially Ligated Fragments by Use of Exonucleases

An exonuclease is needed that can degrade single and double stranded DNA starting from a single stranded nick in double stranded DNA from 3'>5' or 5'>3'. In practice such exonuclease without endonuclease activity is not available, making it necessary to combine several exonucleases. The minimal combination is exonuclease III and exonuclease VII, but we observed that the addition of exonuclease I to the reaction can be driven to completion.

1.7 Opening-Up of the Hairpin-Looped Adapter

A combination of two enzymes, an Uracil-DNA Glycosylase (UDG) and endonuclease VIII, is used for opening the hairpin-looped adapter. Both enzymes have to be heat-labile, that is why the Antarctic UDG is used. Opening-up of the adapter is also beneficial for sodium bisulfite conversion and amplification.

1.8 Optional Sodium Bisulfite Treatment

When DNA is treated with sodium bisulfite all unmethylated cytosines are converted to uracil. In this way DNA-methylation can be investigated. It is most common to use one of the EZ DNA methylation kits distributed by ZymoResearch, because they generate high yields.

1.9 Amplification of the Library

In an optimal embodiment an unbiased high-fidelity polymerase is used (e.g. KAPA Hifi polymerase) and if bisulfite conversion was performed a polymerase has to be used that can readily incorporate nucleotides facing the uracil-bases (e.g. KAPA Hifi Uracil+ polymerase). Primers contain optimally 3'T in a phosphorothioate bond to dampen adapter-dimer amplification.

SEQ ID NO: 8 depicts the sequence of the commercially available NEBNext adapter without 3' phosporothioate bond:

5'P-GATCGGAAGAGCACACGTCTGAACTCCAGTCUACACTCTTTCC

CTACACGACGCTCTTCCGATCT-3'

SEQ ID NO: 9 and 10 depict commercially available NEBnext amplification primers with necessary features for binding to Illumina-chip, index for multiplexing and features for sequencing

SEQ ID NO: 9:
5'-AATGATACGGCGACCACCGAGATCTACACTCTTTCCCTACACGACGC

TCTTCCGATC*T-3'

SEQ ID NO: 10:
5'-CAAGCAGAAGACGGCATACGAGAT*CGTGAT*GTGACTGGAGTTCAGA

CGTGTGCTCTTCCGATC*T-3'

1.10 C0t-Normalization, Next Gen Sequencing and Data Analysis

The C0t normalization, sequencing and data analysis are performed as in protocols described in the art.

2. Complete Protocol of the Invention

Figure 2:
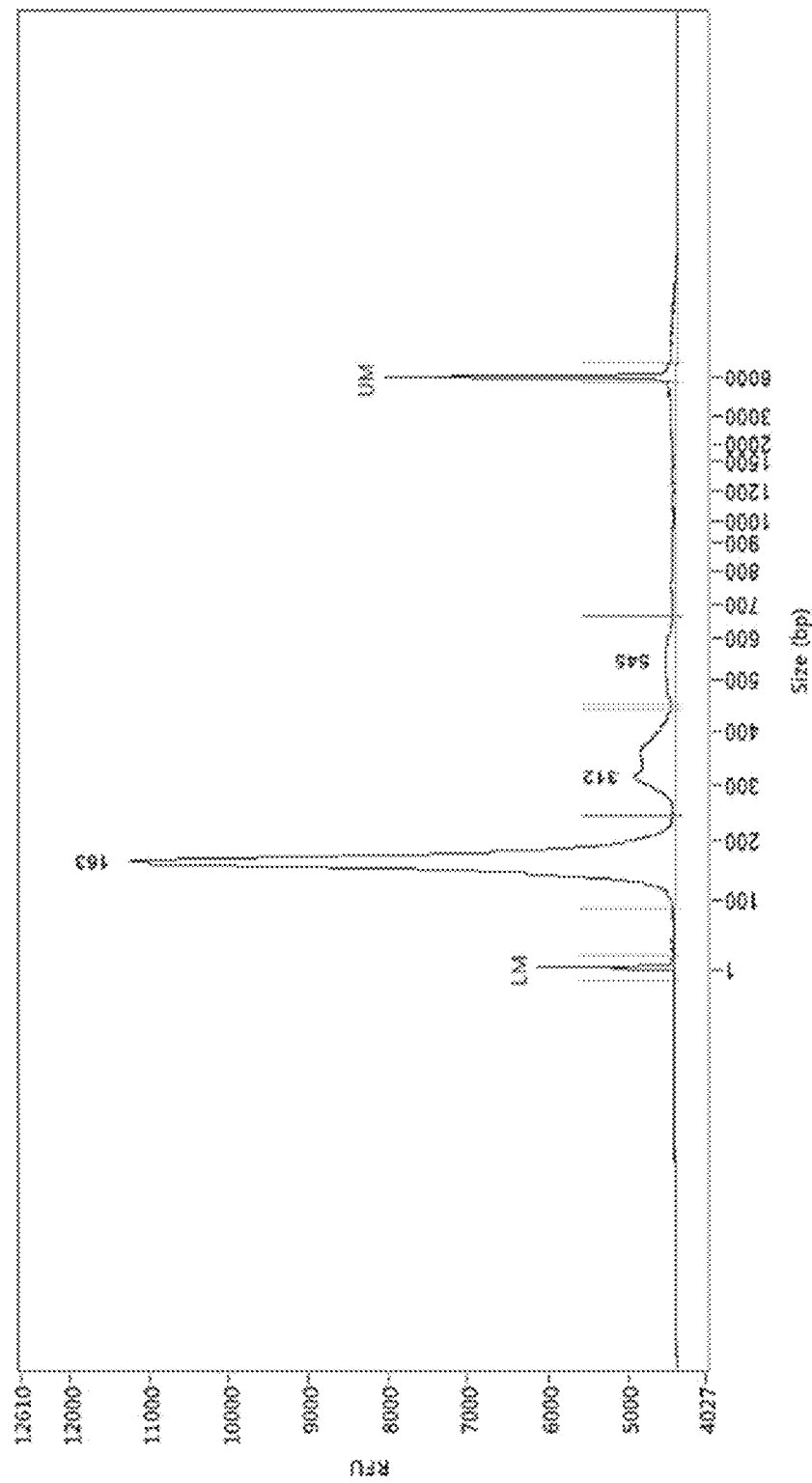
FIG. 2: Electropherogram (Femto Pulse™) of 2 μL cfDNA (±245 pg/μL) from blood plasma of HCC patient uzg002. In total ±428.75 ng cfDNA was extracted from 5 mL blood plasma, starting from 10 mL whole blood drawn in a PAXgene Blood cfDNA Tube (PreAnalytiX). 163 bp-312 bp-545 bp=apoptotic pattern of cfDNA. LM=lower marker, UM=upper marker.

In the present example we applied the method of the invention with test input nucleic acid sequences which resemble sheared nucleic acid sequences present in a biological sample (see FIG. 1). Since nucleic acid sequences derived from a biological sample consist of heavily degraded apoptotic and necrotic DNA, sheared by nucleases in the biological sample, such as blood (see FIG. 2) we used artificial DNA-fragments, which contain two MspI-restriction sites for which the sequence is depicted in SEQ ID NO: 11.

SEQ ID NO: 11 depicts the test DNA which is used for amplification. The two MspI sites are underlined.

SEQ ID NO: 11:

5'-CGCCAGGGTTTTCCCAGTCACGACTACCCGACCACACGGCGTTGAT

CGCCGAGGA<u>CCGG</u>CGTTTCACGTCGACCGAGCTGCGCGACGCGGTCTAC

-continued

GGCGCCGCGGCGGCGCTGATCGCCCTCGGTGTCGAACCCGCAGA<u>CCGGG</u>

TGGCCATCTGGTTCCTGTGTGAAATTGTTATCCGCT-3'

Figure 3:
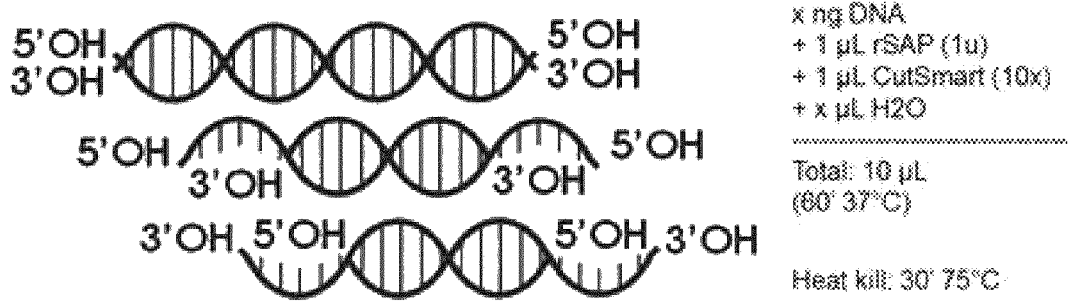
FIG. 3: Enzymatic conditions to dephosphorylate the 5'P-end of the nucleic acid sequences. A cartoon-representation of the generated DNA-products is shown.

Step 1:

The 5' phosphate groups present on 10 ng test nucleic acid sequence (SEQ ID NO: 11) are removed by a suitable DNA phosphatase. The recombinant Shrimp Alkaline Phosphatase (rSAP) was used (source: New England Biolabs). After the dephosphorylation step the enzyme was heat denatured (or heat killed) (75° C. for 30 minutes). FIG. 3 depicts the dephosphorylation reaction.

Figure 4:
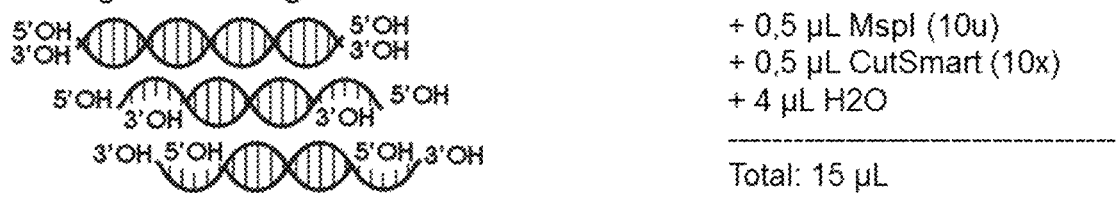
FIG. 4: Restriction digest with MspI. Cartoon-representation of all DNA-products generated: non-digested, digested only at one side, digested at both sides.
Figure 4:
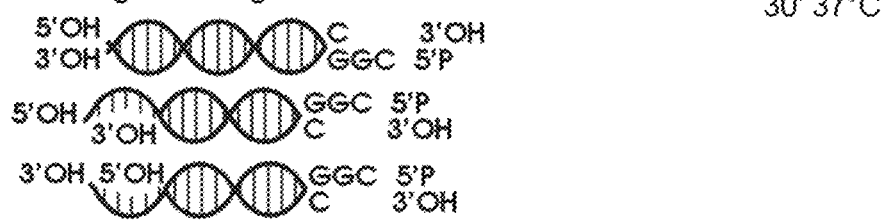
Figure 4:
Figure 5:
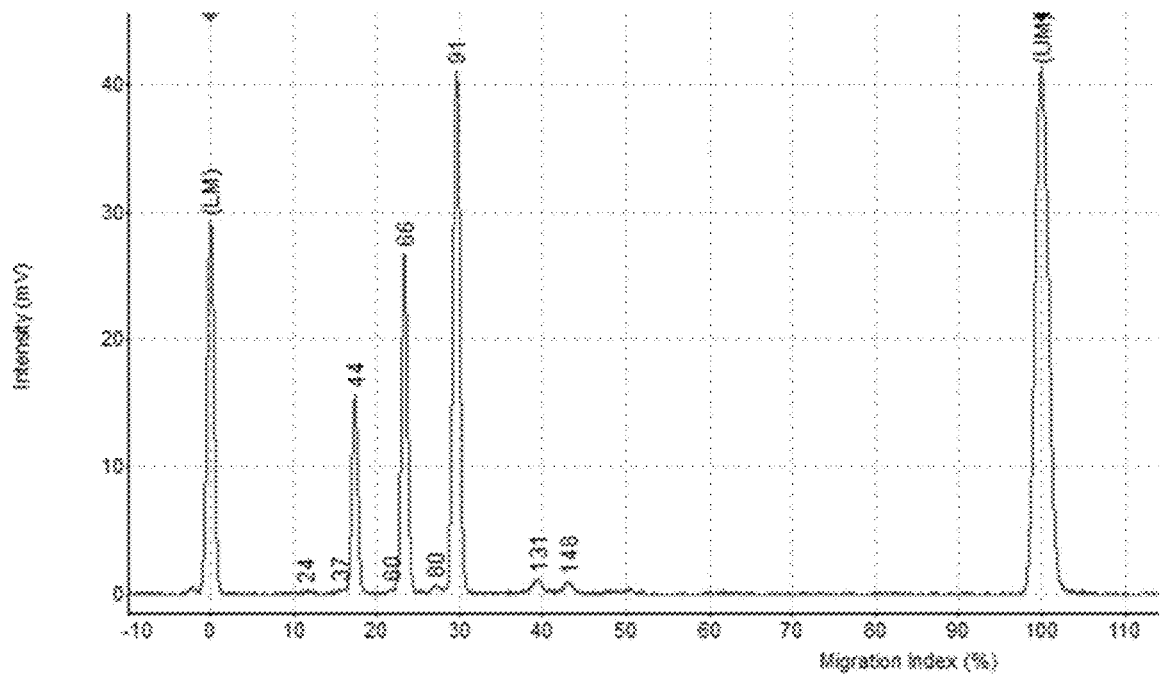
FIG. 5: The dephosphorylated fragment of test DNA (10 ng) was digested with the restriction endonuclease MspI, generating three fragments, two fragments which contains only one MspI end, 40(44) bp and 56(66) bp, and one fragment which contains two MspI ends, 84(91) bp. The detection is carried out with capillary electrophoresis. The length of the observed fragment length is indicated between brackets. For example 84(91) bp means that the real length is 84 bp but is observed in the electrophoresis method as a 91 bp fragment.

Step 2:

In a next step the dephosphorylated nucleic acid sequences are cleaved with a suitable restriction enzyme. In the present example we used the MspI enzyme. MspI is a methylation-insensitive enzyme which is often used in the Reduced Representation Bisulfite Sequencing (RRBS) technology (Gu, H. et al. (2011) Nat. Protoc. 6, 468-481). This technology can be specifically used to enrich CG-rich parts of the genome, thereby reducing the amount of sequencing reads required to capture a major part of the methylome. Methylation state changes, especially hypomethylation, is seen in a lot of cancer types, so focusing on this known relevant piece of the genome could already detect cancer more sensitively. The DNA-fragments can be non-digested, digested at one side or digested at both sides. The latter fragments are the more informative pieces and we will try to use only these further on. FIG. 4 depicts a cartoon representation of the resulted outcome after the MspI cleavage of the nucleic acid sequences. FIG. 5 depicts the MspI digested input material.

Step 3: Fill-in and dA-Tailing with Klenow (Exo-) Polymerase

Figure 6:
FIG. 6: Klenow(exo-) fill in and dA-tailing step
Figure 6:
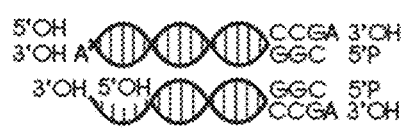
Figure 6:

The 3'OH-ends which are not generated by MspI digestion are not inactivated (meaning that these ends can still participate in the subsequent adapter ligation reaction but will contain a nick) and will also take part in fill-in step and subsequent dA-tailing by use of the Klenow(exo-) in combination with all dNTP's (Km=1-2 μM). A dA-tailed fragment has the advantage that it is compatible with commercially used Illumina-kind adapters. FIG. 6 depicts a cartoon representation of the Klenow (exo-) reaction.

Step 4: Adapter Ligation

Figure 7:
FIG. 7: Ligation reaction to commercial NEBNext adapter (not containing 3' phosporothioate bonds) with T4 DNA ligase
Figure 7:
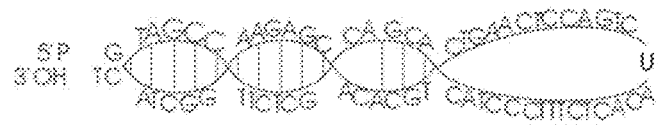
Figure 7:
Figure 7:
Figure 8:
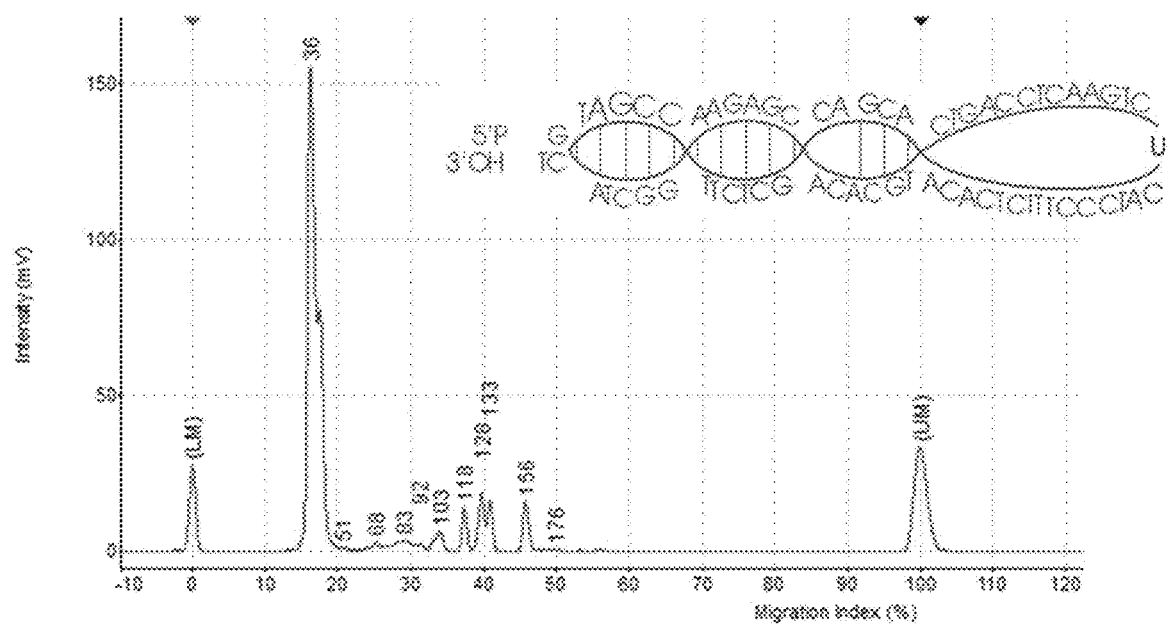
FIG. 8: The three fragments were ligated by T4 DNA ligase to a hairpin-looped adapter (distributed by New England Biolabs, but ordered at Integrated DNA Technologies with no 3' phosphorothioate bond as this blocks exonuclease activity). Fragments annotated are the adapter at 36 bp, the 56 bp fragment ligated to 1×36 bp at 103 bp, the 40 bp fragment ligated to 2×36 bp at 118 bp, the 84 bp fragment ligated to 1×36 bp at 128 bp, the 56 bp fragment ligated to 2×36 bp at 133 bp, the 84 bp fragment ligated to 2×36 bp at 156 bp

An adapter is subsequently ligated to the fragments (here a commercially available adapter from NEB is used), but without phosphorothioate bonds (necessary for the next step using exonucleases). Because the 3'OH-ends, not generated by MspI digestion, are not inactivated and also become dA-tailed, an adapter can ligate to this end, which would eventually generate unwanted non-blocked sequences. High concentration of adapter may cause more background, but can improve the diversity of the library, especially when there is a low amount of input DNA. FIG. 7 depicts a cartoon representation of the adapter ligation. FIG. 8 depicts the adapter-ligation products.

Step 5: Removal of Nicked Ligation Products by Exonucleases I, III and VII

Figure 9:
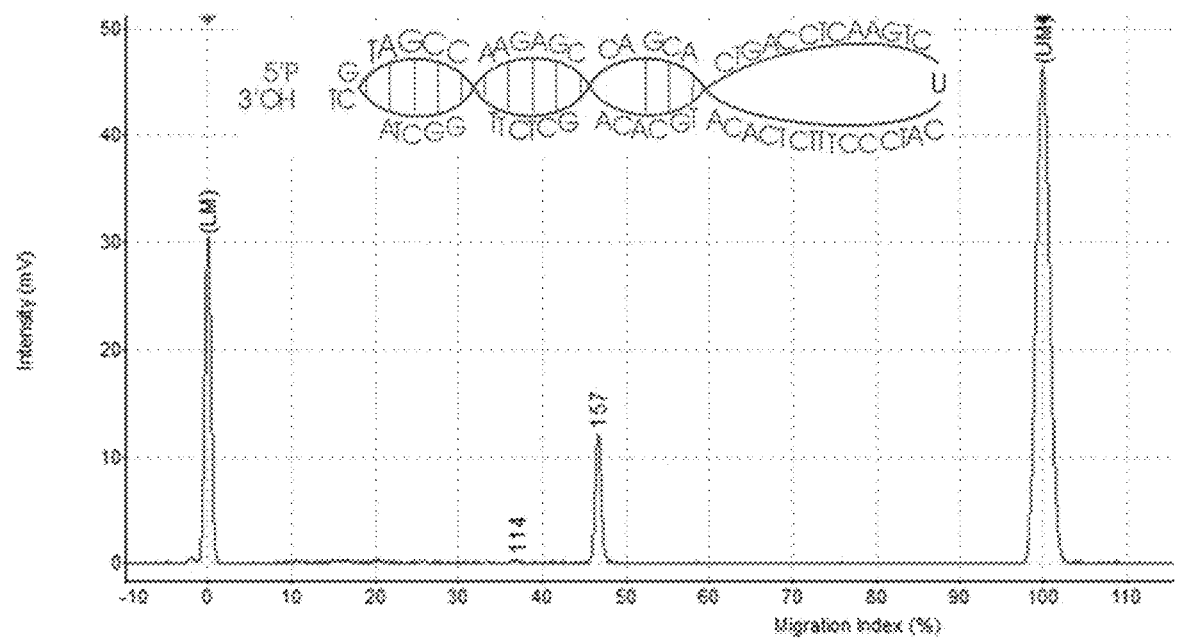
FIG. 9: The mixture of non-, incompletely- and completely-ligated fragments treated with a combination of exonuclease I, exonuclease III and exonuclease VII. The 156(160) bp fragment is left untouched (it is not degraded) because a complete DNA circle is generated, without any nicks.

Only the DNA-fragments which were digested at both sides by MspI will be ligated completely to the adapters. The DNA-fragments which were not digested or digested only at one side will only partially be ligated to the adapters. This is because of the phosphatase treatment in step 1 there is a nick between the adapter and the ligated nucleic acid fragment at these sites. This nick can be recognized by exonuclease III and will be extended to a gap until a piece of ssDNA is formed. This piece is recognized by the second exonuclease, exoVII, which will degrade this. Next to these 2 exonucleases, a third exonuclease, exoI is used, to also degrade ssDNA. All three enzymes can be heat denatured. FIG. 9 depicts the obtained ligation fragments after the Exonuclease digestion step.

Step 6: Opening of the Looped Adapter Cut the Looped Adapter by an UDG and Endo VIII In a next step the looped adapter—nucleic acid ligation products (looped adapter—nucleic acid) are opened by the enzyme Uracil-DNA Glycosylase (UDG) followed by the removal of the nucleic acid fragments having a free 3'- and 5'-end available by Exonuclease VIII. In our experimental setting we used antarctic thermolabile UDG (AnUDG) in the commercial USER-mix of NEB. The mix of AnUDG and endoVIII can be heat denatured and the enzymes are active in the KAPA-buffer.

Step 7: PCR Amplification

Before carrying out the PCR amplification, Solid Phase Reversible Immobilisation beads (SPRI) are used to deplete the remaining adapters and salt. Optionally a bisulfite conversion kit is used before the PCR amplification reaction. Several kits are commercially available such as the EpiTect Fast bisulfite kit from Qiagen or the bisulfite kits from Zymo Research. PCR-amplification is carried out by the Kapa HiFi (U+) polymerase because it is the most unbiased polymerase now available.

Figure 10:
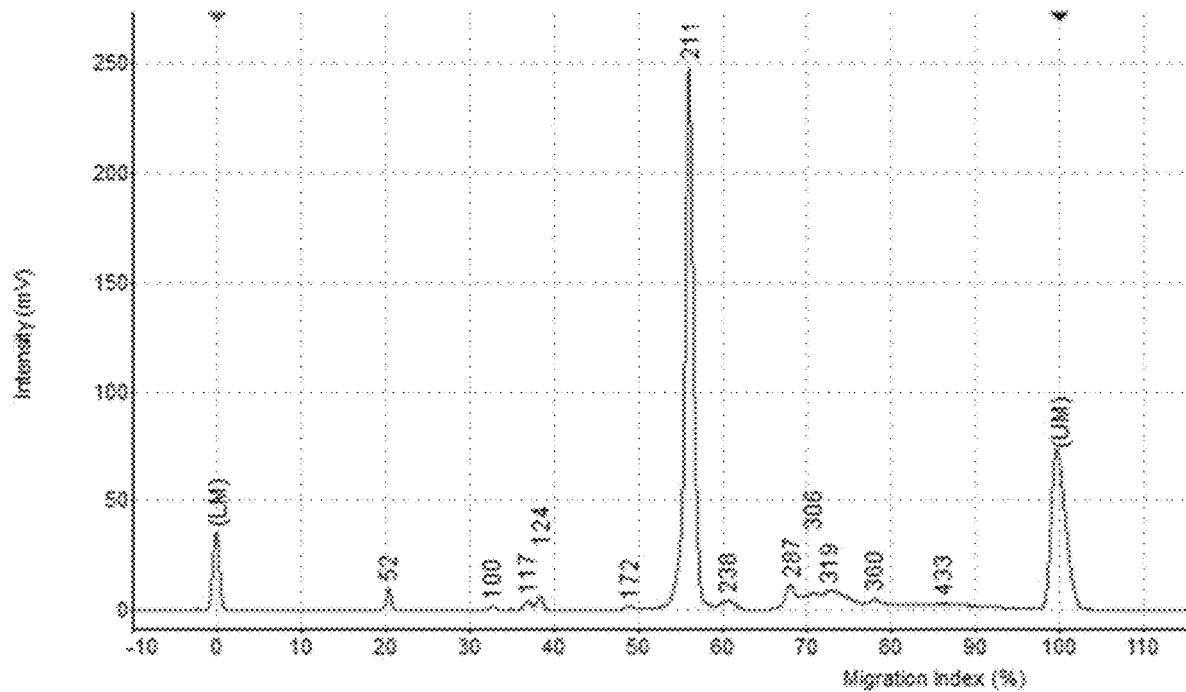
FIG. 10: Starting from 10 ng of the test DNA fragment and performing all steps in the preparation method, this is the final amplification product, which is the 84 bp fragment with a 60 bp adapter sequence at both ends, generating a 204(211) bp fragment.
Figure 11:
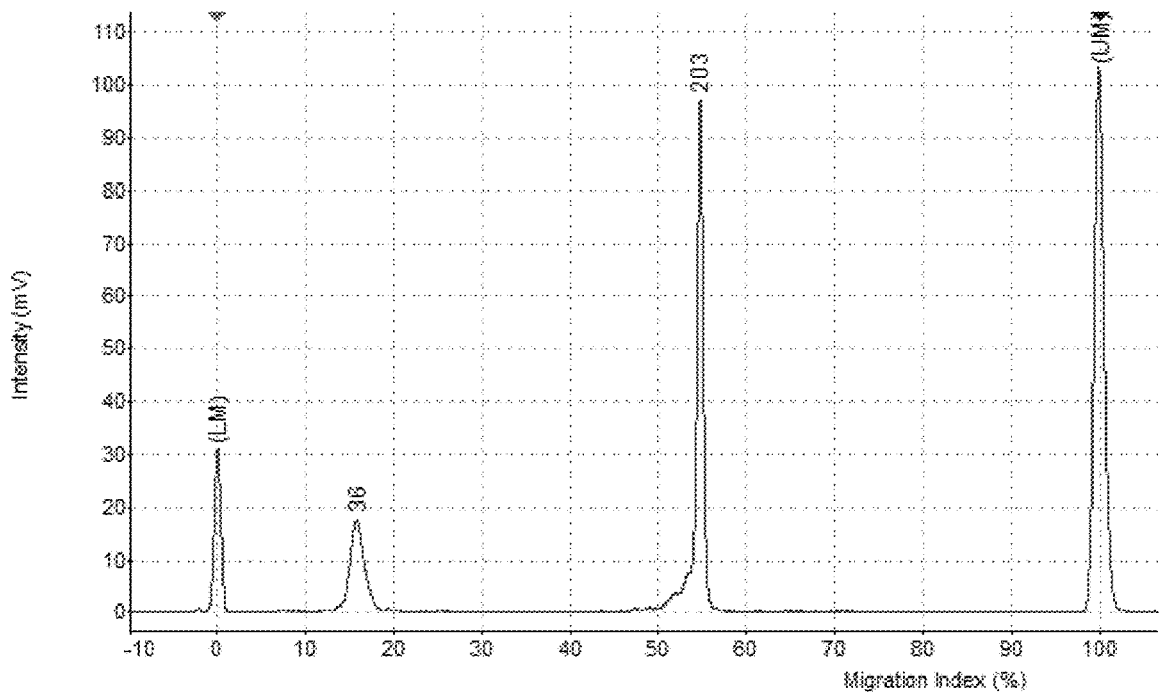
FIG. 11: Complete protocol of the invention with bisulfite conversion (EZ DNA Methylation-Lightning™ Kit (ZymoResearch)) and after PCR-amplification adding Illumina-sequences (commercial NEBNext)
Figure 12:
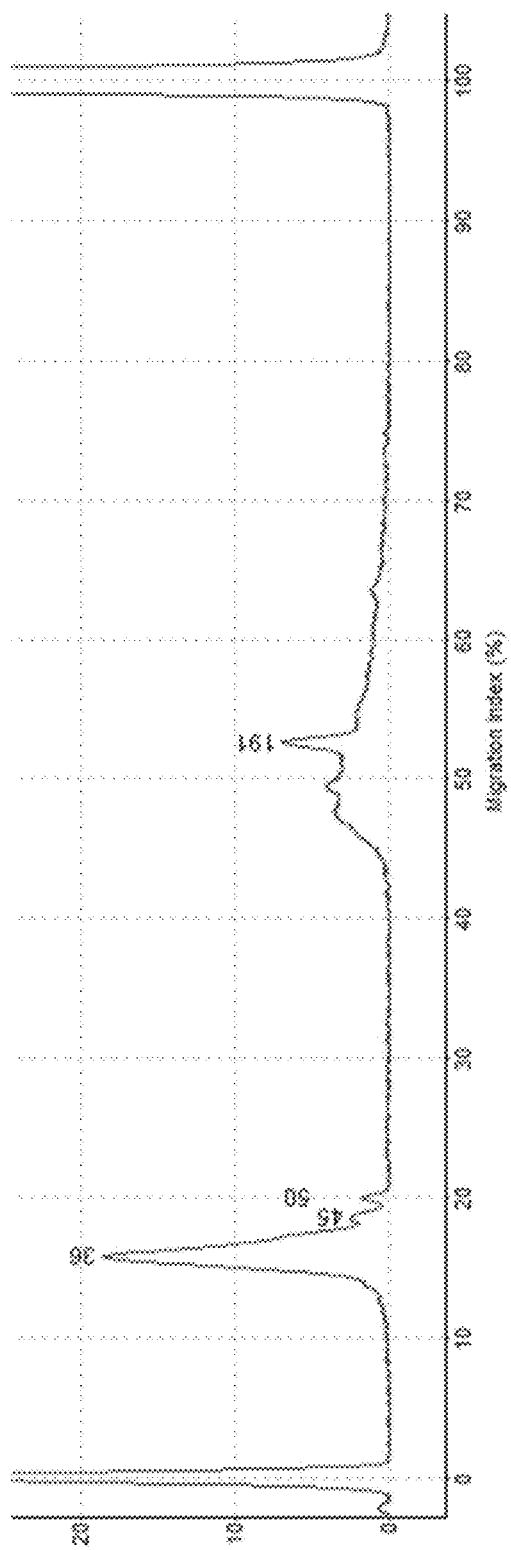
FIG. 12: Complete protocol of the invention (without bisulfite conversion) performed on old, >3 ng 200 bp sheared HEK293S gDNA. Peak at 191 bp can be a highly repetitive piece of the AluY or AluS sequence.
Figure 13:
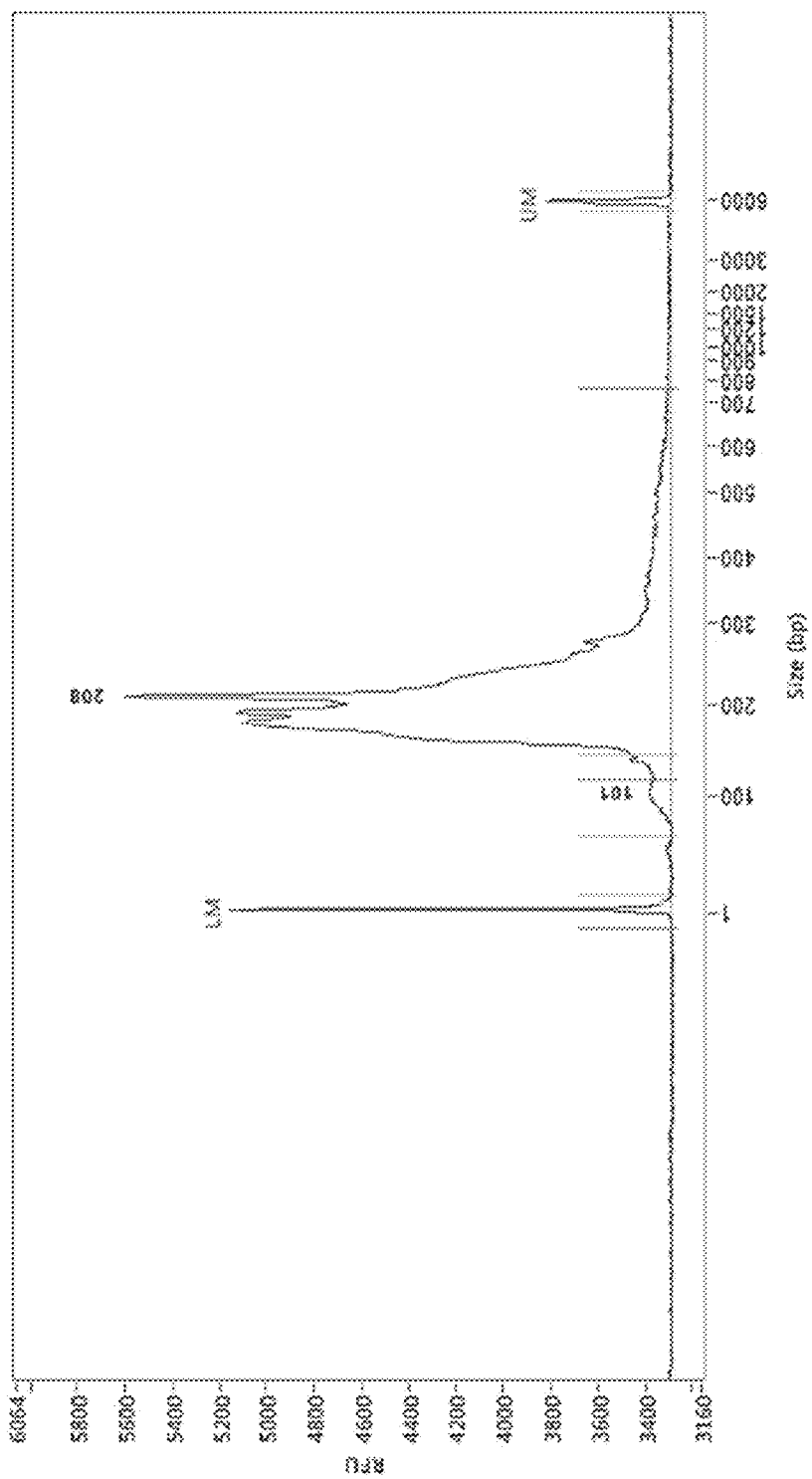
FIG. 13: Electropherogram (Fragment Analyzer™) of the sequencing library prepared by the RRBS amplification protocol on 10 cfDNA of HCC patient uzg002. LM=lower marker, UM=upper marker. Annotation of 101 bp and 208 bp is done by ProSize software but irrelevant

FIG. 10 depicts the PCR-amplified products. FIG. 11 depicts the PCR-amplified products after bisulfite conversion. FIG. 12 depicts a PCR-amplified sequencing library obtained from the artificial input DNA. FIG. 13 depicts PCR-amplified sequencing library obtained from the amplification on 10 ng cfDNA of HCC patient uzg002 according to the steps 1-7 of the protocol.

5. All Amplification Steps can be Carried Out in One Tube

Blood is drawn in STRECK or PreAnalytiX vacutainers. Blood plasma is prepared according to the SOP of the EDRN(NIH). Circulating free DNA is isolated by use of the Quick-cfDNA™ Serum & Plasma Kit according to the instructions given by ZymoResearch Between 1-10 ng input DNA, also 0.1% (of the input DNA concentration) unmethylated lambda-DNA (as an internal standard to test bisulfite conversion efficiency)

---

+1 μL rSAP (NEB) (1u)
+1 μL CutSmart ™ (NEB) (10x)
+8 μL nuclease-free H2O

10 μL reaction

---

60' 37° C.
30' 75° C.

---

+0.5 μL MspI (NEB) (10u)
+0.5 μL CutSmart ™ (NEB) (10x)
+4 μL nuclease-free H2O
15 μL reaction

---

30' 37° C.

---

+0.5 μL Klenow(exo-) (NEB) (5u)
+1 μL CutSmart ™ (NEB) (10x)
+0.25 μL dNTP (0.4 mM dCTP, dGTP, dTTP and 4 mM dATP) (Promega)

|   |
|---|
| +8.25 µL nuclease-free H2O |
| 25 µL reaction |

20' 30° C.
20' 37° C.
30' 75° C.

|   |
|---|
| +1 µL adapter (10 µM) (IDT) |
| +1 µL CutSmart ™ (NEB) (10x) |
| +4 µL ATP (10 mM) |
| +4 µL nuclease-free H2O |
| 35 µL reaction |

|   |
|---|
| +0.5 µL T4 DNA ligase (NEB) (1u) |
| +0.5 µL CutSmart ™ (NEB) (10x) |
| +4 µL nuclease-free H2O |
| 40 µL reaction |

16 h 16° C.
20' 65° C.

|   |
|---|
| +0.5 µL exoI (NEB) (20u) |
| +0.5 µL exoIII (NEB) (50u) |
| +0.5 µL exoVII (NEB) (10u) |
| +0.5 µL CutSmart ™ (NEB) (10x) |
| +3 µL nuclease-free H2O |
| 45 µL reaction |

2 h 37° C.
20' 95° C.

|   |
|---|
| +1 µL AnUDG (NEB) (1u) |
| +0.5 µL endoVIII (NEB) (5u) |
| +0.5 µL CutSmart ™ (NEB) (10x) |
| +3 µL nuclease-free H2O |
| 50 µL reaction |

1 h 37° C.
20' 75° C.

Optionally use 20 µL (40% of the sample) as input for sodium bisulfite treatment (follow EZ DNA methylation Lightning kit as instructed by the company ZymoResearch), use 20 µL (40% of the sample) without sodium bisulfite treatment.

|   |
|---|
| 15 µL KAPA Hifi (uracil+) 2X mix (KAPA Biosystems) |
| 0.9 µL 10 µM universal primer (IDT) |
| 0.9 µL 10 µM indexed primer (IDT) |
| 13.2 µL DNA |
| 30 µL reaction |

1×5' 95° C.
15-25×20" 98° C.
15-25×15" 65° C.
15-25×15" 72° C.
1×5' 72° C.

C0t normalization is performed according to protocols which are available in the art.

For example, combine the DNA library with 4× hybridization buffer and denature for 2' 98° C., let renature for 5 h-21 h at 68° C. Add preheated (68° C.) 2×DSN buffer and add the DSN enzyme. Incubate this mixture for 25' at 68° C. Amplify.

The invention claimed is:

1. A method to amplify sheared DNA with an average length of less than 200 nucleotides, the method comprising:
    obtaining a sample comprising sheared DNA,
    dephosphorylating the sheared DNA,
    digesting the dephosphorylated DNA with at least one sequence specific DNA cutting tool to generate digested polynucleotides,
    ligating the digested polynucleotides to hairpin looped adapters,
    removing incompletely ligated products, and
    amplifying the resulting ligated polynucleotides using primers hybridizing to the adapters.

2. The method according to claim 1, wherein ligating the digested polynucleotides is preceded by a treatment of the digested polynucleotides with Klenow polymerase and Klenow exo-minus polymerase or with Klenow exo-minus polymerase in the presence of deoxynucleotide bases.

3. The method according to claim 1, wherein the incompletely ligated products are removed by adding exonuclease I, III, and VII to the sample.

4. The method according to claim 1, further comprising enzymatically opening the hairpin looped adapters before amplification.

5. The method according to claim 1, wherein digesting is carried out with a methylation insensitive restriction enzyme.

6. The method according to claim 1, further comprising treating the ligated polynucleotides with bisulphite before amplification.

7. The method according to claim 1, wherein the sample comprising sheared DNA is a patient blood, serum, or plasma sample.

8. A kit for amplifying sheared DNA with an average length of less than 200 nucleotides, the kit comprising:
    a DNA phosphatase,
    at least one restriction enzyme,
    exonucleases I, III, and VII,
    Klenow enzyme,
    Klenow exo-minus enzyme,
    deoxynucleotide bases,
    hairpin looped adapters,
    primers specific for the hairpin looped adapters,
    a DNA polymerase, and
    a buffer system.

* * * * *